United States Patent
Zhao

(10) Patent No.: US 7,084,169 B2
(45) Date of Patent: Aug. 1, 2006

(54) AMINOALKOXYINDOLES AND METHODS OF USE

(75) Inventor: Shu-Hai Zhao, Sunnyvale, CA (US)

(73) Assignee: Roche Palo Alto LLC, Palo Alto, CA (US)

(*) Notice: Subject to any disclaimer, the term of this patent is extended or adjusted under 35 U.S.C. 154(b) by 271 days.

(21) Appl. No.: 10/724,683

(22) Filed: Dec. 1, 2003

(65) Prior Publication Data

US 2004/0132799 A1    Jul. 8, 2004

Related U.S. Application Data

(60) Provisional application No. 60/430,506, filed on Dec. 3, 2002.

(51) Int. Cl.
*A61K 31/40* (2006.01)
*C07D 209/36* (2006.01)

(52) U.S. Cl. ............... 514/418; 548/465; 548/484

(58) Field of Classification Search ............... 514/418, 514/414, 417; 548/465, 484
See application file for complete search history.

(56) References Cited

U.S. PATENT DOCUMENTS

| 4,582,905 A | 4/1986 | Sakai |
|---|---|---|
| 4,977,274 A | 12/1990 | Descamps et al. |
| 5,254,595 A | 10/1993 | Guzzi et al. |
| 6,284,277 B1 | 9/2001 | Bouloumie et al. |
| 6,310,074 B1 | 10/2001 | Depreux et al. |
| 6,319,930 B1 | 11/2001 | Lesieur et al. |
| 6,509,357 B1 | 1/2003 | Zhou et al. |

FOREIGN PATENT DOCUMENTS

| WO | WO 98/08817 A1 | 3/1998 |
|---|---|---|
| WO | WO 00/46198 A1 | 8/2000 |
| WO | WO 02/059088 A1 | 8/2002 |
| WO | WO 02/085853 A2 | 10/2002 |

*Primary Examiner*—Kamal A. Saeed
(74) *Attorney, Agent, or Firm*—Robert C. Hall

(57) ABSTRACT

The invention provides compound of the Formula:

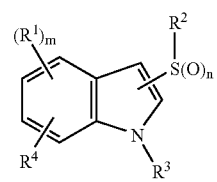

and pharmaceutically acceptable salts or prodrugs thereof, wherein $R^1$, $R^2$, $R^3$, $R^4$, m and n are as defined herein. The invention also provides methods for preparing, compositions comprising, and methods for using compounds of formula I.

50 Claims, No Drawings

AMINOALKOXYINDOLES AND METHODS OF USE

CROSS REFERENCE TO RELATED APPLICATIONS

This application is entitled to the benefit of U.S. Provisional Patent Application Ser. No. 60/430,506 filed on Dec. 3, 2002, the disclosure of which is incorporated herein by reference.

FIELD OF THE INVENTION

This invention relates to aminoalkoxyindoles and associated compositions, methods for use as therapeutic agents, and methods of preparation thereof.

BACKGROUND OF THE INVENTION

The actions 5-hydroxytryptamine (5-HT) as a major modulatory neurotransmitter in the brain, are mediated through a number of receptor families termed 5-HT1, 5-HT2, 5-HT3, 5-HT4, 5-HT5, 5-HT6, and 5-HT7. Based on a high level of 5-HT6 receptor mRNA in the brain, it has been stated that the 5-HT6 receptor may play a role in the pathology and treatment of central nerve system disorders. In particular, 5-HT2-selective and 5-HT6 selective ligands have been identified as potentially useful in the treatment of certain CNS disorders such as Parkinson's disease, Huntington's disease, anxiety, depression, manic depression, psychoses, epilepsy, obsessive compulsive disorders, mood disorders, migraine, Alzheimer's disease (enhancement of cognitive memory), sleep disorders, feeding disorders such as anorexia, bulimia and obesity, panic attacks, akathisia, attention deficit hyperactivity disorder (ADHD), attention deficit disorder (ADD), withdrawal from drug abuse such as cocaine, ethanol, nicotine and benzodiazepines, schizophrenia, and also disorders associated with spinal trauma and/or head injury such as hydrocephalus. Such compounds are also expected to be of use in the treatment of certain gastrointestinal (GI) disorders such as functional bowel disorder. See for example, B. L. Roth et al., *J. Pharmacol. Exp. Ther.*, 1994, 268, pages 1403–14120, D. R. Sibley et al., *Mol. Pharmacol.*, 1993, 43, 320–327, A. J. Sleight et al., *Neurotransmission*, 1995, 11, 1–5, and A. J. Sleight et al., *Serotonin ID Research Alert*, 1997, 2(3), 115–8.

While many 5-hydroxytryptamine modulators have been disclosed, there continues to be a need for compounds that are useful for modulating 5-HT2, 5-HT6 and other 5-HT receptors.

SUMMARY OF THE INVENTION

The invention provides substituted indole compounds of the formula I:

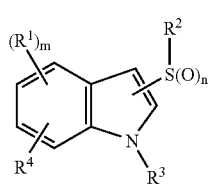

or pharmaceutically acceptable salts, solvates or prodrugs thereof, wherein:

m is from 0 to 3;

n is from 0 to 2;

each $R^1$ is independently hydrogen, halo, alkyl, haloalkyl, hydroxy, heteroalkyl, nitro, alkoxy, cyano, $-NR^aR^b$, $-S(O)_s-R^a$, $-C(=O)-NR^aR^b$, $-SO_2-NR^aR^b$, $-N(R^a)-C(=O)-R^b$, or $-C(=O)-R^a$, where each of $R^a$ and $R^b$ is independently hydrogen or alkyl, or two of $R^1$ may form an alkylene or alkylene dioxy group;

$R^2$ is aryl or heteroaryl;

$R^3$ is hydrogen or alkyl; and $R^4$ is of the formula:

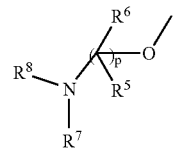

wherein:

p is 2 or 3; and $R^5$, $R^6$, $R^7$ and $R^8$ each independently is hydrogen or alkyl, or one of $R^5$ and $R^6$ together with one of $R^7$ and $R^8$ and the atoms therebetween may form a heterocyclic ring of 4 to 7 members, or $R^7$ and $R^8$ together with their shared nitrogen may form a heterocyclic ring of 4 to 7 members; or one of $R^7$ and $R^8$ together with $R^3$ and the atoms therebetween may form a heterocyclic ring of 4 to 7 members.

Methods for making substituted indoles in accordance with the invention are also provided, the methods comprising:

(a) contacting an indole of the formula a:

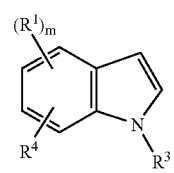

wherein:

m, $R^1$, $R^3$, and $R^4$ are as described herein;

with a disulfide of the formula $R^2-S-S-R^2$ where $R^2$ is as described herein, to produce a sulfanylated indole of the formula b:

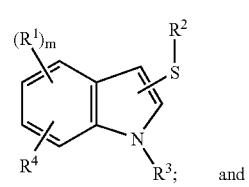

and (b) optionally oxidizing the sulfanylated indole b to produce a substituted indole of the formula I:

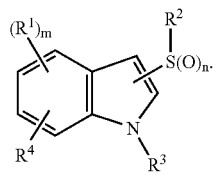

The invention further provides pharmaceutical compositions and methods of treatment of subjects suffering from central nervous system diseases and 5-hydroxytryptamine receptor-mediated conditions generally, and for treatment of subjects suffering from gastrointestinal tract disorders. These and other objects and advantages of the invention will be made clear in the following detailed description.

DETAILED DESCRIPTION OF THE INVENTION

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Agonist" refers to a compound that enhances the activity of another compound or receptor site.

"Alkyl" means a monovalent linear or branched saturated hydrocarbon moiety, consisting solely of carbon and hydrogen atoms, having from one to twelve carbon atoms. "Lower alkyl" refers to an alkyl group of one to six carbon atoms, preferably one to four carbon atoms. Examples of alkyl groups include, but are not limited to, methyl, ethyl, propyl, isopropyl, isobutyl, sec-butyl, tert-butyl, pentyl, n-hexyl, octyl, dodecyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, 2,2-dimethylbutylene, pentylene, and the like.

"Alkylene dioxy" means a divalent radical of the formula —O—R—O— wherein R is alkylene as defined herein. Alkylene dioxy includes methylene dioxy, ethylene dioxy, and the like.

"Alkoxy" means a moiety of the formula —OR$^Z$, wherein R$^Z$ is an alkyl moiety as defined herein. Examples of alkoxy moieties include, but are not limited to, methoxy, ethoxy, isopropoxy, and the like.

"Optionally substituted", when used in association with "aryl", phenyl", "heteroaryl" or "heterocyclyl", means an aryl, phenyl, heteroaryl or heterocyclyl which is optionally substituted independently with one to four substituents, preferably one or two substituents selected from alkyl, cycloalkyl, cycloalkylalkyl, heteroalkyl, hydroxyalkyl, halo, nitro, cyano, hydroxy, alkoxy, amino, acylamino, mono-alkylamino, di-alkylamino, haloalkyl, haloalkoxy, heteroalkyl, —COR (where R is hydrogen, alkyl, phenyl or phenylalkyl, —(CR'R")$_n$—COOR (where n is an integer from 0 to 5, R' and R" are independently hydrogen or alkyl, and R is hydrogen, alkyl, cycloalkyl, cycloalkylalkyl, phenyl or phenylalkyl), or —CR'R")$_n$—CONR$^a$R$^b$ (where n is an integer from 0 to 5, R' and R" are independently hydrogen or alkyl, and R$^a$ and R$^b$ are, independently of each other, hydrogen, alkyl, cycloalkyl, cycloalkylalkyl, phenyl or phenylalkyl). These substituents can form a 5- to 7-membered fused ring system containing 0 to 3 heteroatoms. The fused ring system in turn may be optionally substituted with alkyl, oxo, cyano or alkoxy.

"Heterocyclylalkyl" means a radical R$^a$—R$^b$—where R$^a$ is a heterocyclyl group as defined herein and may be optionally substituted, and R$^b$ is an alkylene group as defined herein.

"Heterocyclyloxy" means a radical R$^a$—O— where R$^a$ is a heterocyclyl group as defined herein and may optionally be substituted. "Heterocyclyloxy" includes, by way of example, piperidin-4-yl-oxy, piperidin-3-yl-oxy, pyrrolidin-3-yl-oxy, and the like.

"Heterocyclylalkyloxy" means a radical R$^a$—R$^b$—O— where R$^a$ is a heterocyclyl group as defined herein and may be optionally substituted, and R$^b$ is an alkylene group as defined herein. "Heterocyclylalkyloxy" includes, by way of example, pyrrolidin-1-yl-methoxy pyrrolidin-2-yl-methoxy, pyrrolidin-3-yl-methoxy, pyrrolidin-1-yl-ethoxy, pyrrolidin-2-yl-ethoxy, pyrrolidin-3-yl-ethoxy, pyrrolidin-1-yl-propyloxy, pyrrolidin-2-yl-propyloxy, pyrrolidin-3-yl-propyloxy, pyrrolidin-1-yl-isopropyloxy, pyrrolidin-2-yl-isopropyloxy, pyrrolidin-3-yl-isopropyloxy, piperidine-4-yl-methoxy, piperidine-3-yl-methoxy, piperidine-2-yl-methoxy, piperidine-1-yl-methoxy, piperidine-4-yl-ethoxy, piperidine-3-yl-ethoxy, piperidine-2-yl-ethoxy, piperidine-1-yl-ethoxy, piperidine-4-yl-propyloxy, piperidine-3-yl-propyloxy, piperidine-2-yl-propyloxy, piperidine-1-yl-propyloxy, piperidine-4-yl-isopropyloxy, piperidine-3-yl-isopropyloxy, piperidine-2-yl-isopropyloxy, piperidine-1-yl-isopropyloxy, piperazin-1-yl-methoxy, piperazin-2-yl-methoxy, piperazin-1-yl-ethoxy, piperazin-2-yl-ethoxy, piperazin-1-yl-propyloxy, piperazin-2-yl-propyloxy, piperazin-1-yl-isopropyloxy, piperazin-2-yl-isopropyloxy, azetidin-3-yl-methoxy, azetidin-3-yl-ethoxy, azetidin-1-yl-ethoxy, aziridin-2-yl-methoxy, aziridin-2-yl-ethoxy, aziridin-1-yl-ethoxy, and the like.

"Heteroalkyl" means an alkyl radical as defined herein with one, two or three substituents independently selected from —OR$^a$, —NR$^b$R$^c$, and —S(O)$_n$R$^d$ (where n is an integer from 0 to 2), with the understanding that the point of attachment of the heteroalkyl radical is through a carbon atom of the heteroalkyl radical. R$^a$ is hydrogen, alkyl, cycloalkyl, cycloalkyl-alkyl, aryl, aralkyl, alkoxycarbonyl, aryloxycarbonyl, carboxamido, or mono- or di-alkylcarbamoyl. R$^b$ is hydrogen, alkyl, cycloalkyl, cycloalkyl-alkyl, aryl or aralkyl. R$^c$ is hydrogen, alkyl, cycloalkyl, cycloalkyl-alkyl, aryl, aralkyl, alkoxycarbonyl, aryloxycarbonyl, carboxamido, mono- or di-alkylcarbamoyl or alkylsulfonyl. R$^d$ is hydrogen (provided that n is 0), alkyl, cycloalkyl, cycloalkyl-alkyl, aryl, aralkyl, amino, mono-alkylamino, di-alkylamino, or hydroxyalkyl. Representative examples include, for example, 2-hydroxyethyl, 2,3-dihydroxypropyl, 2-methoxyethyl, benzyloxymethyl, 2-methylsulfonyl-ethyl.

"Aminoalkyl" means a radical of the formula R$^a$R$^b$N—R$^c$— where R$^a$ and R$^b$ are hydrogen or alkyl as defined herein, and R$^c$ is alkylene as defined herein.

"Aminoalkoxy" or "Aminoalkyloxy" means a radical of the formula R$^a$R$^b$N—R$^c$—O—where R$^a$ and R$^b$ are hydrogen or alkyl as defined herein, and R$^c$ is alkylene as defined herein. "Aminoalkoxy" includes, by way of example, aminoethoxy, aminopropyloxy, N-methylaminoethoxy, N-ethylaminoethoxy, N-propylaminoethoxy, N-isopropylaminoethoxy, N,N-dimethylaminoethoxy, N-methyl-N-ethylaminoethoxy, N-methyl-N-propylaminoethoxy, N-methyl-N-isopropylaminoethoxy, N,N-diethylaminoethoxy, N-ethyl-N-propylaminoethoxy, N-ethyl-N-isopropylaminoethoxy, N,N-dipropylaminoethoxy, N,N-diisopropylaminoethoxy, aminopropyloxy, N-methylaminopropyloxy, N-ethylaminopropyloxy, N-propylaminopropyloxy, N-isopropylaminopropyloxy, N,N-dimethylaminopropyloxy, N-methyl-N-ethylaminopropyloxy, N-methyl-N-propylaminopropyloxy, N-methyl-N-isopropylaminopropyloxy, N,N-diethylaminopropyloxy, N-ethyl-N-propylaminopropyloxy, N-ethyl-N-isopropylaminopropyloxy, N,N-dipropylaminopropyloxy, N,N-diisopropylaminopropyloxy, aminoisopropyloxy, N-methylaminoisopropyloxy, N-ethylaminoisopropyloxy, N-propylaminoisopropyloxy, N-isopropylaminoisopropyloxy, N,N-dimethylaminoisopropyloxy, N-methyl-N-ethylaminoisopropyloxy, N-methyl-N-propylaminoisopropyloxy, N-methyl-N-isopropylaminoisopropyloxy, N,N-diethylaminoisopropyloxy, N-ethyl-N-propylaminoisopropyloxy, N-ethyl-N-isopropylaminoisopropyloxy, N,N-dipropylaminoisopropyloxy, N,N-diisopropylaminoisopropyloxy, and the like.

"Antagonist" refers to a compound that diminishes or prevents the action of another compound or receptor site.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, optionally substituted phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially and fully hydrogenated derivatives thereof.

"Cycloalkyl" means a monovalent saturated carbocyclic moiety consisting of mono- or bicyclic rings. Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkyl moieties include, but are not limited to, cyclopropyl, cyclobutyl, cyclopentyl, cyclohexyl, cycloheptyl, cyclooctyl and the like.

"Disease state" means any disease, condition, symptom, or indication.

The terms "halo" and "halogen", which may be used interchangeably herein, refer to a substituent fluoro, chloro, bromo, or iodo.

"Haloalkyl" means alkyl as defined herein in which one or more hydrogen has been replaced with same or different halogen. Exemplary haloalkyls include —CH$_2$Cl, —CH$_2$CF$_3$, —CH$_2$CCl$_3$, perfluoroalkyl (e.g., —CF$_3$), and the like.

"Heteroaryl" means a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. Heteroaryl can be optionally substituted as defined herein. In addition, a substituted heteroaryl also includes a cycloalkyl and/or a heterocyclyl group that is fused to the heteroaryl moiety. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, benzothienyl, thiophenyl, furanyl, pyranyl, pyridyl, pyrrolyl, pyrazolyl, pyrimidyl, quinolinyl, isoquinolinyl, benzofuryl, benzothiophenyl, benzothiopyranyl, benzimidazolyl, benzooxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially and fully hydrogenated derivatives thereof.

"Heterocyclyl" and "heterocyclic" mean a saturated moiety, consisting of one to three rings, incorporating one, two, or three heteroatoms (chosen from nitrogen, oxygen or sulfur). The heterocyclyl ring may be optionally substituted as defined herein. Examples of heterocyclyl moieties include, but are not limited to, piperidinyl, piperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiamorpholinyl, thiamorpholinylsulfoxide, thiamorpholinylsulfone, dihydroquinolinyl, dihydrisoquinolinyl, tetrahydroquinolinyl, tetrahydrisoquinolinyl, and the like.

"Leaving group" means the group with the meaning conventionally associated with it in synthetic organic chemistry, i.e., an atom or group displaceable under substitution reaction conditions. Examples of leaving groups include, but are not limited to, halogen, hydroxy, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include:

acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

The preferred pharmaceutically acceptable salts are the salts formed from acetic acid, hydrochloric acid, sulfuric acid, methanesulfonic acid, maleic acid, phosphoric acid, tartaric acid, citric acid, sodium, potassium, calcium, zinc, and magnesium.

It should be understood that all references to pharmaceutically acceptable salts include solvent addition forms (solvates) or crystal forms (polymorphs) as defined herein, of the same acid addition salt.

The terms "pro-drug" and "prodrug", which may be used interchangeably herein, refer to any compound which releases an active parent drug according to formula I in vivo when such prodrug is administered to a mammalian subject. Prodrugs of a compound of formula I are prepared by modifying one or more functional group(s) present in the compound of formula I in such a way that the modification(s) may be cleaved in vivo to release the parent compound. Prodrugs include compounds of formula I wherein a hydroxy, amino, or sulfhydryl group in a compound of Formula I is bonded to any group that may be cleaved in vivo to regenerate the free hydroxyl, amino, or sulftydryl group, respectively. Examples of prodrugs include, but are not limited to, esters (e.g., acetate, formate, and benzoate derivatives), carbamates (e.g., N,N-dimethylaminocarbonyl) of hydroxy functional groups in compounds of formula I, N-acyl derivatives (e.g. N-acetyl) N-Mannich bases, Schiff bases and enaminones of amino functional groups, oximes, acetals, ketals and enol esters of ketone and aldehyde functional groups in compounds of Formula I, and the like, see Bundegaard, H. "Design of Prodrugs" p1–92, Elesevier, New York-Oxford (1985), and the like.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. Similarly, the term "hydroxy protecting group" refers to those organic groups intended to protect the oxygen atom of a hydroxyl group against undesirable reactions during synthetic procedures. Exemplary hydroxy protecting groups include, but are not limited to, benzyl, silyl groups, tetrahydropyranyl, esters, and the like. The artisan in the art will know how to choose a group for the ease of removal and for the ability to withstand the following reactions.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The terms "those defined above" and "those defined herein" when referring to a variable incorporates by reference the broad definition of the variable as well as preferred, more preferred and most preferred definitions, if any.

"Treating" or "treatment" of a disease state includes:
(i) preventing the disease state, i.e. causing the clinical symptoms of the disease state not to develop in a subject that may be exposed to or predisposed to the disease state, but does not yet experience or display symptoms of the disease state.
(ii) inhibiting the disease state, i.e., arresting the development of the disease state or its clinical symptoms, or
(iii) relieving the disease state, i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature

In general, the nomenclature used in this Application is based on AUTONOM™ v.4.0, a Beilstein Institute computerized system for the generation of IUPAC systematic nomenclature. For convenience, the IUPAC numbering of the positions of the indole compounds disclosed herein is shown by the formula:

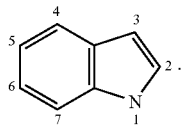

Compounds of the Invention

The invention provides substituted indole compounds having an aminoalkoxy, heterocyclylalkyloxy or heterocyclyloxy group at any of positions 4- through 7-, and an aryl- or heteroaryl-sufonyl, sulfinyl or sulfanyl group at position 2- or 3- of the indole system, as well as pharmaceutically acceptable salts or prodrugs thereof. The subject compounds are of the formula I:

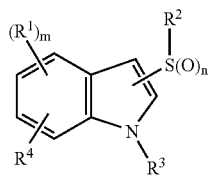

or pharmaceutically acceptable salts or prodrugs thereof, wherein:

m is from 0 to 3; preferably m is 0 or 1;
n is from 0 to 2; preferably n is 0 or 2;
each $R^1$ is independently hydrogen, halo, alkyl, haloalkyl, hydroxy, heteroalkyl, nitro, alkoxy, cyano, —$NR^aR^b$, —$S(O)_s$—$R^a$, —$C(=O)$—$NR^aR^b$, —$SO_2$—$NR^aR^b$, —$N(R^a)$—$C(=O)$—$R^b$, or —$C(=O)$—$R^a$, where each of $R^a$ and $R^b$ is independently hydrogen or alkyl, or two of $R^1$ may form an alkylene or alkylene dioxy group;
$R^2$ is aryl or heteroaryl; preferably $R^2$ is optionally substituted phenyl;
$R^3$ is H or alkyl; and:
$R^4$ is of the formula:

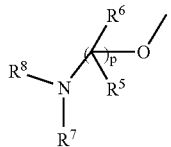

wherein:

p is 2 or 3; more preferably p is 2; and
$R^5$, $R^6$, $R^7$ and $R^8$ each independently is hydrogen or alkyl, or one of $R^5$ and $R^6$ together with one of $R^7$ and $R^8$ and the atoms therebetween may form a ring of 4 to 7 members, or
$R^7$ and $R^8$ together with their shared nitrogen may form a ring of 4 to 7 members, or one of $R^7$ and $R^8$ together with $R^3$ and the atoms therebetween may form a heterocyclic ring of 4 to 7 members. Where any of $R^1$, $R^2$, $R^3$, $R^4$, $R^5$, $R^6$, $R^7$ and $R^8$ are alkyl, they are preferably lower alkyl, i.e. $C_1$–$C_6$ alkyl, and more preferably $C_1$–$C_4$ alkyl.

It should be understood that the scope of this invention encompasses not only the various isomers which may exist but also the various mixture of isomers which may be formed. Furthermore, the scope of the present invention also encompasses solvates and salts of compounds of formula I.

In certain embodiments, n is 0 or 2, and $R^2$ is 2-halophenyl, 3-halopheny, 4-halophenyl, 2,3-dihalophenyl, 2,4-dihalophenyl, 3,4-dihalophenyl, 2,5-dihalophenyl, 2-alkoxyphenyl, 3-alkoxypheny, 4-alkoxyphenyl, 2,3-dialkoxyphenyl, 2,4-dialkoxyphenyl, 3,4-dialkoxyphenyl, or 2,5-dialkoxyphenyl; In specific embodiments $R^2$ is 2-chlorophenyl, 3-chlorophenyl, 4-chlorophenyl, 2,3-dichlorophenyl, 3,4-dichlorophenyl, 2,5-dichlorophenyl, 2-fluororophenyl, 3-fluororophenyl, 2-methoxyphenyl or 3-methoxyphenyl.

In certain embodiments, $R^4$ may be pyrrolidin-1-yl-methoxy pyrrolidin-2-yl-methoxy, pyrrolidin-3-yl-methoxy, pyrrolidin-1-yl-ethoxy, pyrrolidin-2-yl-ethoxy, pyrrolidin-3-yl-ethoxy, pyrrolidin-1-yl-propyloxy, pyrrolidin-2-yl-propyloxy, pyrrolidin-3-yl-propyloxy, pyrrolidin-1-yl-isopropyloxy, pyrrolidin-2-yl-isopropyloxy, pyrrolidin-3-yl-isopropyloxy, piperidine-4-yl-methoxy, piperidine-3-yl-methoxy, piperidine-2-yl-methoxy, piperidine-1-yl-methoxy, piperidine-4-yl-ethoxy, piperidine-3-yl-ethoxy, piperidine-2-yl-ethoxy, piperidine-1-yl-ethoxy, piperidine-4-yl-propyloxy, piperidine-3-yl-propyloxy, piperidine-2-yl-propyloxy, piperidine-1-yl-propyloxy, piperidine-4-yl-isopropyloxy, piperidine-3-yl-isopropyloxy, piperidine-2-yl-isopropyloxy, piperidine-1-yl-isopropyloxy, piperazin-1-yl-methoxy, piperazin-2-yl-methoxy, piperazin-1-yl-ethoxy, piperazin-2-yl-ethoxy, piperazin-1-yl-propyloxy, piperazin-2-yl-propyloxy, piperazin-1-yl-isopropyloxy, piperazin-2-yl-isopropyloxy, azetidin-3-yl-methoxy, azetidin-3-yl-ethoxy, azetidin-1-yl-ethoxy, aziridin-2-yl-methoxy, aziridin-2-yl-ethoxy, aziridin-1-yl-ethoxy, azepin-2-yl-methoxy, azepin-2-yl-ethoxy, azepin-3-yl-methoxy, azepin-3-yl-ethoxy, azepin-1-yl-ethoxy, aminoethoxy, aminopropyloxy, N-methylaminoethoxy, N-ethylaminoethoxy, N-propylaminoethoxy, N-isopropylaminoethoxy, N,N-dimethylaminoethoxy, N-methyl-N-ethylaminoethoxy, N-methyl-N-propylaminoethoxy, N-methyl-N-isopropylaminoethoxy, N,N-diethylaminoethoxy, N-ethyl-N-propylaminoethoxy, N-ethyl-N-isopropylaminoethoxy, N,N-dipropylaminoethoxy, N,N-diisopropylaminoethoxy, aminopropyloxy, N-methylaminopropyloxy, N-ethylaminopropyloxy, N-propylaminopropyloxy, N-isopropylaminopropyloxy, N,N-dimethylaminopropyloxy, N-methyl-N-ethylaminopropyloxy, N-methyl-N-propylaminopropyloxy, N-methyl-N-isopropylaminopropyloxy, N,N-diethylaminopropyloxy, N-ethyl-N-propylaminopropyloxy, N-ethyl-N-isopropylaminopropyloxy, N,N-dipropylaminopropyloxy, N,N-diisopropylaminopropyloxy, aminoisopropyloxy, N-methylaminoisopropyloxy, N-ethylaminoisopropyloxy, N-propylaminoisopropyloxy, N-isopropylaminoisopropyloxy, N,N-dimethylaminoisopropyloxy, N-methyl-N-ethylaminoisopropyloxy, N-methyl-N-propylaminoisopropyloxy, N-methyl-N-isopropylaminoisopropyloxy, N,N-diethylaminoisopropyloxy, N-ethyl-N-propylaminoisopropyloxy, N-ethyl-N-isopropylaminoisopropyloxy, N,N-dipropylaminoisopropyloxy, or N,N-diisopropylaminoisopropyloxy.

In specific embodiments $R^4$ may be optionally substituted 2-pyrrolidin-1-yl-ethoxy, optionally substituted pyrrolidin-2-methoxy, optionally substituted piperidin-4-yloxy, optionally substituted piperazin-1-yl-ethoxy, optionally substituted azetidin-3-yl-methoxy, aminoethoxy, 2,2-dimethylaminoethoxy, 2-methylaminoethoxy or 2-dimethylaminoethoxy.

Compounds of formula I may also be represented the formula II:

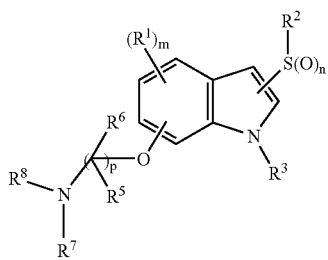

II wherein n, m, p, $R^1$, $R^2$, $R^3$, $R^5$, $R^6$, $R^7$ and $R^8$ are as defined herein. In certain embodiments of formula II, p is 2 and $R^7$ and $R^8$ together with their shared nitrogen may form a pyrolidinyl group. In still other embodiments $R^5$ and $R^7$, together with the intervening carbon and nitrogen, may form an azetidinyl group. In specific embodiments, $R^4$ may be at the 7-position of the indole ring such that compounds of formula I are of the formula III:

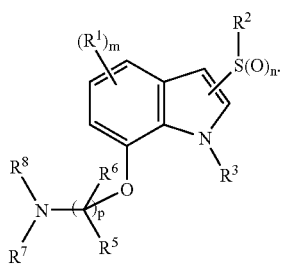

III wherein n, m, p, $R^1$, $R^2$, $R^3$, $R^5$, $R^6$, $R^7$ and $R^8$ are as defined herein. In some embodiments compounds of formula I are of formula IV:

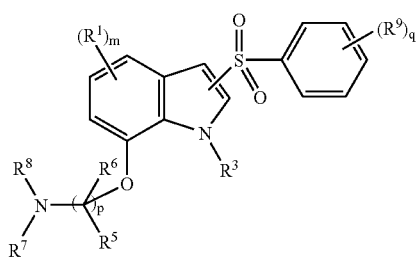

IV wherein m, p, $R^1$, $R^3$, $R^5$, $R^6$, $R^7$ and $R^8$ again are as defined herein, and wherein q is from 0 to 4 and each $R^9$ is independently hydrogen, halo, alkyl, haloalkyl or alkoxy; preferably q is from 0 to 2 and each $R^9$ is independently hydrogen, halo or alkoxy.

In still other embodiments, the compounds of formula II may be represented by formula V:

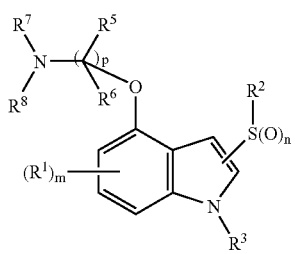

V wherein n, m, p, $R^1$, $R^2$, $R^3$, $R^5$, $R^6$, $R^7$ and $R^8$ are as defined herein. Compounds formula V may in specific embodiments be represented by formula VI:

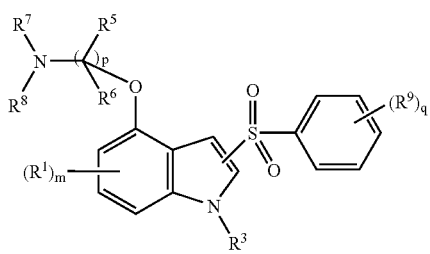

VI wherein n, m, p, q, $R^1$, $R^2$, $R^3$, $R^5$, $R^6$, $R^7$, $R^8$ and $R^9$ again are as defined herein.

Representative compounds in accordance with the invention are shown in Table 1 as hydrochloride salts.

TABLE 1

| | Structure | Name (Autonom ®) | Example | MP, ° C. or M + H |
|---|---|---|---|---|
| 1 | 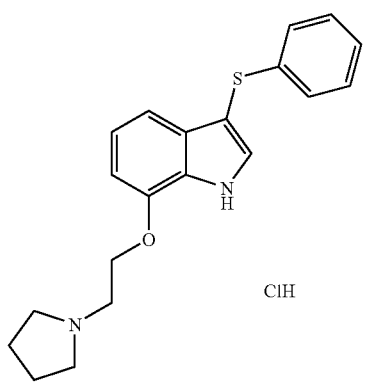 | 3-Phenylsulfanyl-7-(2-pyrrolidin-1-yl-ethoxy)-1H-indole | 1 | 210–213 |

TABLE 1-continued
| Structure | Name (Autonom ®) | Example | MP, ° C. or M + H |
|---|---|---|---|
| 2 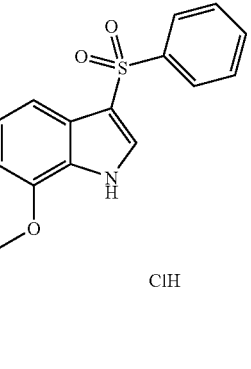 | 3-Benzenesulfonyl-7-(2-pyrrolidin-1-yl-ethoxy)-1H-indole | 1 | 265.1–273.4 |
| 3 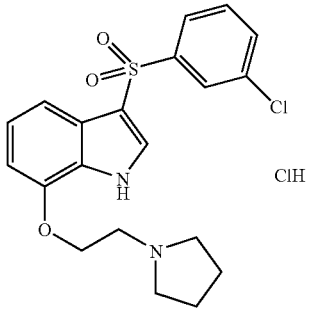 | 3-(3-Chloro-benzenesulfonyl)-7-(2-pyrrolidin-1-yl-ethoxy)-1H-indole | 1 | 257–260.1 |
| 4 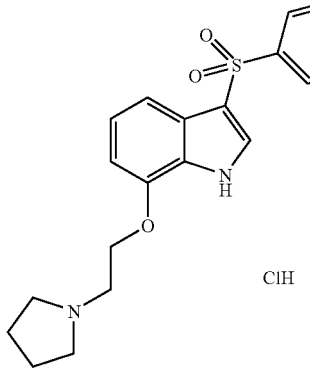 | 3-(4-Chloro-benzenesulfonyl)-7-(2-pyrrolidin-1-yl-ethoxy)-1H-indole | 1 | 406 |
| 5 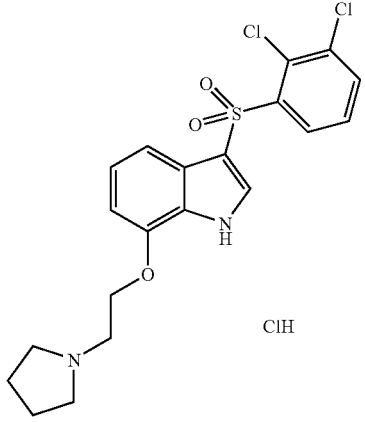 | 3-(2,3-Dichloro-benzenesulfonyl)-7-(2-pyrrolidin-1-yl-ethoxy)-1H-indole | 1 | 260–262.4 |

TABLE 1-continued
| Structure | Name (Autonom ®) | Example | MP, ° C. or M + H |
|---|---|---|---|
| 6 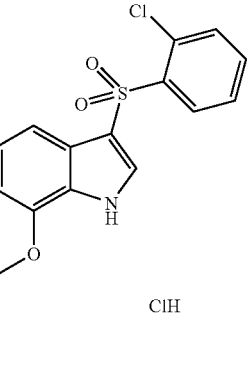 | 3-(2-Chloro-benzenesulfonyl)-7-(2-pyrrolidin-1-yl-ethoxy)-1H-indole | 1 | 406 |
| 7 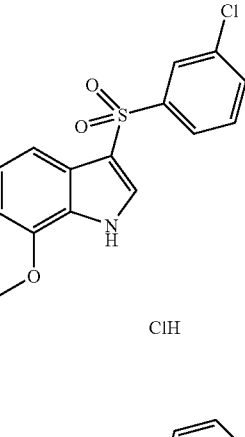 | 3-(3,4-Dichloro-benzenesulfonyl)-7-(2-pyrrolidin-1-yl-ethoxy)-1H-indole | 1 | 257.8–262.9 |
| 8 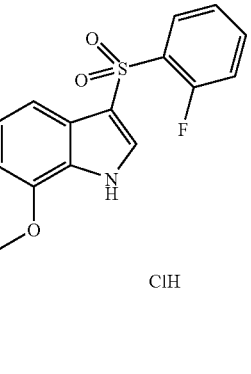 | 3-(2-Fluoro-benzenesulfonyl)-7-(2-pyrrolidin-1-yl-ethoxy)-1H-indole | 1 | 266.7–269.7 |
| 9 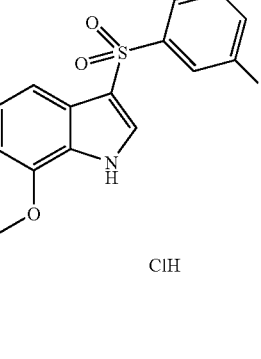 | 3-(3-Fluoro-benzenesulfonyl)-7-(2-pyrrolidin-1-yl-ethoxy)-1H-indole | 1 | 275–279.1 |

TABLE 1-continued

| Structure | Name (Autonom ®) | Example | MP, ° C. or M + H |
|---|---|---|---|
| 10 | 3-(3-Methoxy-benzenesulfonyl)-7-(2-pyrrolidin-1-yl-ethoxy)-1H-indole · ClH | 1 | 89–92 |
| 11 | 3-(2-Methoxy-benzenesulfonyl)-7-(2-pyrrolidin-1-yl-ethoxy)-1H-indole · ClH | 1 | 212–213.9 |
| 12 | [2-(3-Benzenesulfonyl-1H-indol-7-yloxy)-ethyl]-dimethyl-amine · ClH | 1 | 248.5–250.1 |
| 13 | {2-[3-(2-Methoxy-benzenesulfonyl)-1H-indol-7-yloxy]-ethyl}-dimethyl-amine · ClH | 1 | 242.9–245.3 |

TABLE 1-continued
| Structure | Name (Autonom ®) | Example | MP, ° C. or M + H |
|---|---|---|---|
| 14 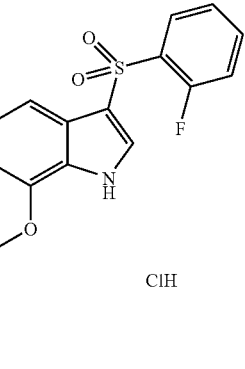 | {2-[3-(2-Fluoro-benzenesulfonyl)-1H-indol-7-yloxy]-ethyl}-dimethyl-amine | 1 | 250–253.8 |
| 15 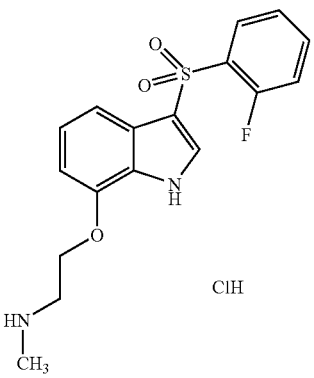 | 2-[3-(2-Fluoro-benzenesulfonyl)-1H-indol-7-yloxy{]-ethyl}-methyl-amine | 2 | 281.7–282.9 |
| 16 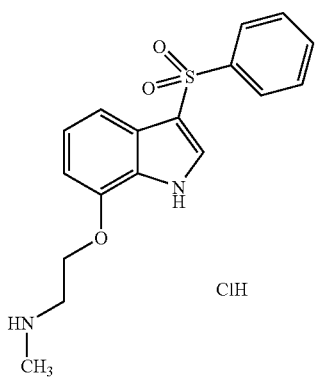 | [2-(3-Benzenesulfonyl-1H-indol-7-yloxy)-ethyl]-methyl-amine | 2 | 270.4–276.1 |
| 17 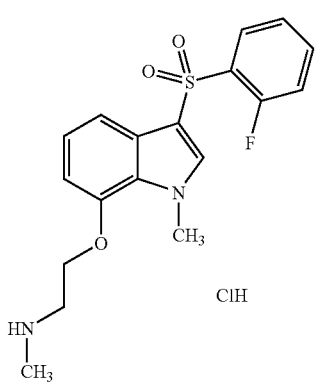 | [2-(3-Benzenesulfonyl-1-methyl-1H-indol-7-yloxy)-ethyl]-methyl-amine | 3 | 225.0–227.3 |

TABLE 1-continued

| Structure | Name (Autonom ®) | Example | MP, ° C. or M + H |
|---|---|---|---|
| 18 | (S)-3-(2-Fluoro-benzenesulfonyl)-7-(pyrrolidin-2-ylmethoxy)-1H-indole | 2 | 255.6–263.7 |
| 19 | 3-Benzenesulfonyl-7-(piperidin-4-yloxy)-1H-indole | 2 | 157.5–164.5 |
| 20 | [2-(2-Benzenesulfonyl-1H-indol-4-yloxy)-ethyl]-methyl-amine | 4 | 250.7–252.1 |
| 21 | [2-(2-Benzenesulfonyl-1H-indol-7-yloxy)-ethyl]-methyl-amine | 5 | 331 |
| 22 | 3-(2,5-Dichloro-benzenesulfonyl)-7-(2-pyrrolidin-1-yl-ethoxy)-1H-indole | 1 | 440 |

TABLE 1-continued

| Structure | Name (Autonom ®) | Example | MP, ° C. or M + H |
|---|---|---|---|
| 23 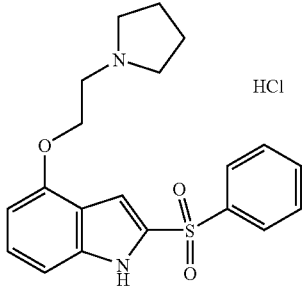 | 2-Benzenesulfonyl-4-(2-pyrrolidin-1-yl-ethoxy)-1H-indole | 6 | 371 |
| 24 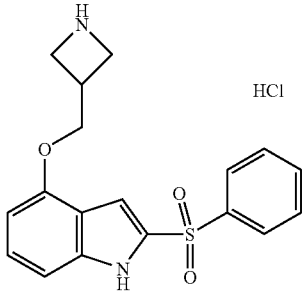 | 4-(Azetidin-3-ylmethoxy)-2-benzenesulfonyl-1H-indole | 6 | 343 |
| 25 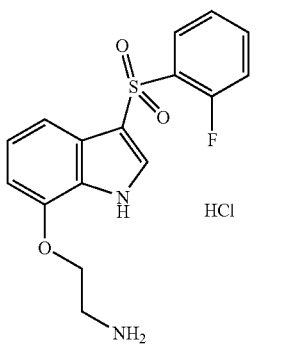 | 2-[3-(2-Fluoro-benzenesulfonyl)-1H-indol-7-yloxy]-ethylamine | 7 | 335 |
| 26 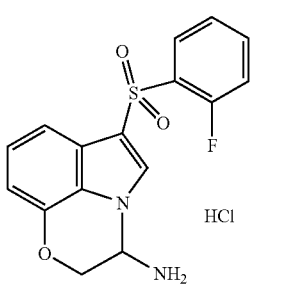 | 1-(2-Fluoro-benzenesulfonyl)-3,4-dihydro-5-oxa-2a-aza-acenaphthylen-3-ylamine | 7 | 333 |

Another aspect of the present invention provides a phamaceutical composition comprising a therapeutically effective amount of at least one compound of formula I in admixture with a pharmaceutically acceptable carrier, diluent, excipient and/or adjuvant.

Yet another aspect of the present invention provides a method for treating a central nervous system (CNS) disease state in a subject comprising administering to the subject a therapeutically effective amount of a compound of formula I. The disease state may comprise, for example, psychoses, schizophrenia, manic depressions, neurological disorders, memory disorders, attention deficit disorder, Parkinson's disease, amyotrophic lateral sclerosis, Alzheimer's disease and Huntington's disease.

Still another aspect of the present invention provides a method for treating a disorder of the gastrointestinal tract in a subject comprising administering to the subject a therapeutically effective amount of a Compound of Formula I.

Another aspect of the present invention provides a method for producing a compound of formula I.

Synthesis

Compounds of the present invention can be made by a variety of methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1–15; *Rodd's Chemistry of Carbon Compounds*, Elsevier Science Publishers, 1989, Volumes 1–5 and Supplementals; and *Organic Reactions*, Wiley & Sons: New York, 1991, Volumes 1–40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about –78° C. to about 150° C., more preferably from about 0° C. to about 125° C., and most preferably and conveniently at about room (or ambient) temperature, e.g., about 20° C.

In one embodiment, compounds of formula I are prepared by the procedure shown in Scheme A, wherein X is a leaving group and n, m, p, $R^1$, $R^2$, $R^3$, $R^4$, $R^5$, $R^6$, $R^7$ and $R^8$ are as described herein. The procedure of Scheme A is preferred for preparation of indoles with —S(O)$_n$—$R^2$ at the 3-position.

SCHEME A

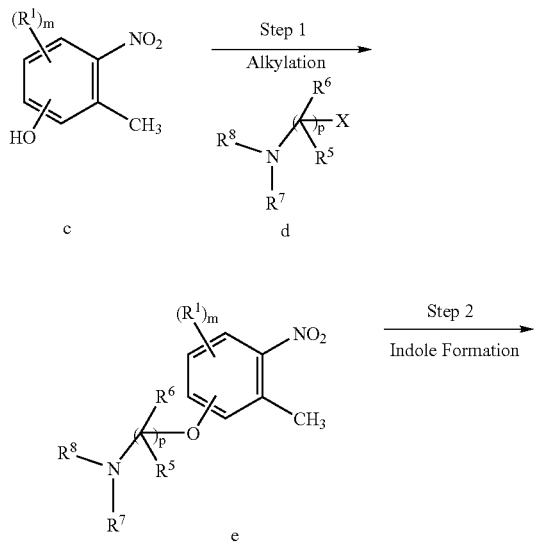

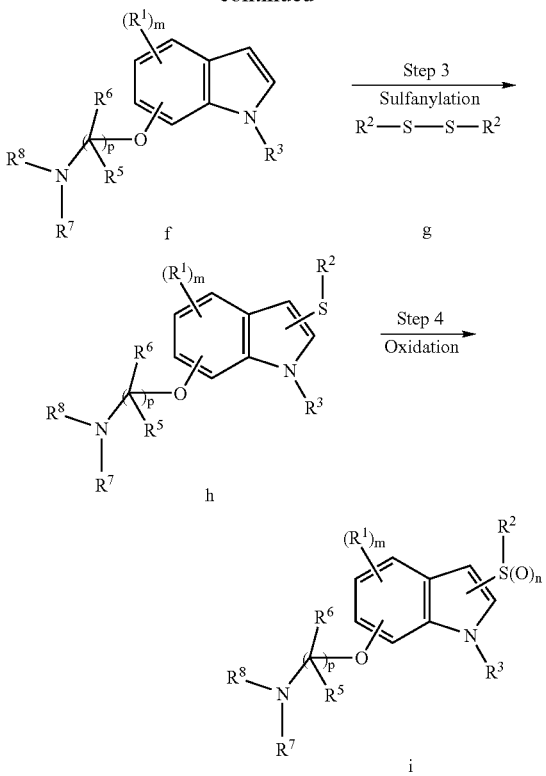

In Step 1 of Scheme A, a phenol O-alkylation is carried out by reacting a methylnitrophenol c with an alkylating agent d. This step may, in some embodiments, involve treatment of a methylnitrophenol c with $K_2CO_3$ or like base under polar solvent conditions to generate a phenolate anion (not shown), followed by treatment with alkylating agent d, wherein X is halo. The presence of iodide may be used to facilitate this alkylation where X is chloro. In other embodiments, leaving group X of alkylating agent d may be hydroxyl, and alkylation of phenol c may be achieved by treatment of phenol c with triphenylphosphine and diethylazodicarboxylate (DEAD) in the presence of alkylating agent d.

Various aminoalkyl, heterocyclylalkyl, and heterocyclyl compounds with suitable leaving groups may be used in Step 1. For example, alkylation with 1-(2-haloethyl)-pyrrolidine provides an alkylating agent d wherein p is 2, $R^5$ and $R^6$ are hydrogen and $R^7$ and $R^8$ form a five-membered pyrrolidine ring. The alkylating agent N-(2-haloethyl)-dimethylamine provides a p equal to 2, with $R^5$ and $R^6$ as hydrogen and $R^7$ and $R^8$ as methyl. Use of 4-halopiperidine as alkylating agent d provides a p of 1, with $R^5$ and $R^7$ as hydrogen, and with $R^6$ and $R^8$ together forming a six-membered piperidine ring. In instances where one or both of $R^7$ and $R^8$ are hydrogen, such as 2-chloroethylamine and 2-chloroethylmethylamine, BOC protection or other suitable protection strategies may be used to protect the nitrogen of compound d in this step and in subsequent steps. See, for example, *Protective Groups in Organic Synthesis*, 3$^{rd}$ edition, T. W. Greene and P. G. M. Wuts, John Wiley & Sons, New York, 1999, which is incorporated herein by reference. Numerous other suitable alkylating agents d will suggest themselves to those skilled in the art and may also be used in Step 1.

In Step 2, indole synthesis is carried out by: (1) reaction of the O-alkyated methylnitrophenol e with dimethylformamide dimethyl acetal (DMFDA) in the presence of base to form a condensation product (not shown); and (2) reduction of the nitro group on the condensation product to a corresponding amine to effect ring closure and provide the indole compound f. The condensation product is not isolated in Step 2, but is reduced in situ to allow ring closure for indole formation. Both condensation and reduction in this step may be carried out under polar solvent conditions. The in situ reduction may be achieved by addition of Pt or Pd catalyst on activated carbon in the presence of a hydrogen source such as potassium formate to provide the condensation product.

In Step 3, indole f prepared in Step 2 is sulfanylated by treatment with a disulfide $R^2$—S—S—$R^2$ g in the presence of metal hydride or like base under dry polar aprotic solvent conditions to provide a sulfanylated indole compound h. $R^2$ may be aryl or heteroaryl as noted above, depending upon the particular embodiment desired. Many aryl disulfides and heteroaryl disulfides are available using known synthetic techniques and may be used in this Step to obtain sulfanylated indole compound h.

In Step 4, sulfanylated indole h may optionally be oxidized using a peracid, OXON®, or like oxidizing agent to provide a substituted indole i wherein n is 1 (sulfinyl) or 2 (sulfonyl)

Numerous variations on the above procedure will suggest themselves to those skilled in the art upon review of this disclosure. For example, O-alkylation may be carried out subsequent to formation of the indole ring as shown in the Examples below. Also, indole synthesis may be achieved via well-known routes other than that used in Step 2. The number, functionality and/or location of the $R^1$ substituent groups may be selected to facilitate O-alkylation of phenolic hydroxyl groups at selected positions as desired for specific embodiments of the subject compounds.

Compounds of formula I may also be prepared by the procedure shown in Scheme B, wherein m, p, $R^1$, $R^2$, $R^3$, $R^4$, $R^5$, $R^6$, $R^7$ and $R^8$ are as described herein. The procedure of Scheme B is preferred for preparation of indole compounds with —S(O)$_n$—$R^2$ at the 2-position.

SCHEME B

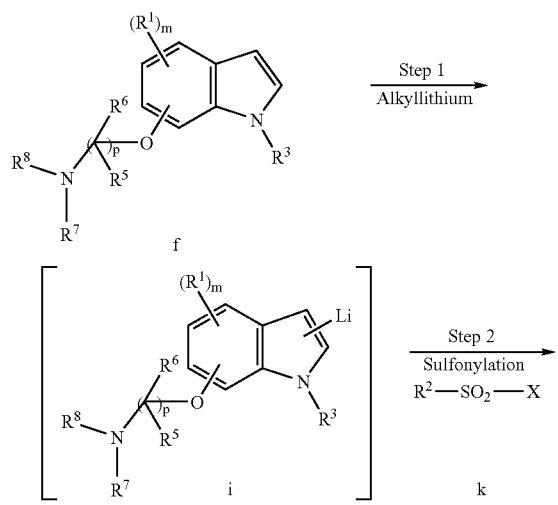

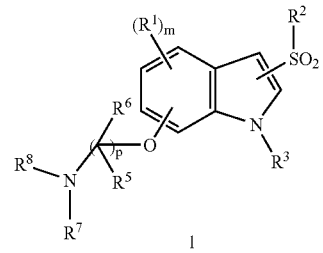

Indole compound f as used in Step 1 of Scheme B may be prepared as described above for Scheme A or by other synthetic technique. In this Scheme, $R^3$ is alkyl or a removable protecting group, and also serves as a directing group for lithiation.

In Step 1 of Scheme B, indole compound f is treated with an alkyllithium reagent or other strong base under anhydrous polar aprotic conditions and dry ice/acetone temperature to generate a corresponding indole-lithium compound i by deprotonation at the 2- or 3-position. Where $R^4$ is hydrogen, a suitable removable protecting group may be used to protect the indole nitrogen of compound f. Indole-lithium compound i is not isolated but is used directly in Step 2.

In Step 2, an arylsulfonyl halide or heteroarylsulfonyl halide k (X is preferably fluoro in this step) is added directly to indole-lithium compound i to provide substituted indole l. As in the case of Scheme A, many variations in the synthetic procedure shown in Scheme B may suggest themselves to those skilled in the art upon review of this disclosure, and such synthetic procedures may also be used in accordance with the invention.

More specific details for producing compounds of formula I are described in the Examples section.

Utility

The compounds of the invention have selective affinity for 5-HT receptors, including 5-HT6, and as such are expected to be useful in the treatment of certain CNS disorders such as Parkinson's disease, Huntington's disease, anxiety, depression, manic depression, psychosis, epilepsy, obsessive compulsive disorders, mood disorders, migraine, Alzheimer's disease (enhancement of cognitive memory), sleep disorders, feeding disorders such as anorexia, bulimia, and obesity, panic attacks, akathisia, attention deficit hyperactivity disorder (ADHD), attention deficit disorder (ADD), withdrawal from drug abuse such as cocaine, ethanol, nicotine and benzodiazepines, schizophrenia, and also disorders associated with spinal trauma and/or head injury such as hydrocephalus. Such compounds are also expected to be of use in the treatment of certain GI (gastrointestinal) disorders such functional bowel disorder and irritable bowel syndrome.

Testing

The pharmacology of the compounds of this invention was determined by art-recognized procedures. The in vitro techniques for determining the affinities of test compounds at the 5-HT6 receptor in radioligand binding and functional assays are described in the Examples below.

Administration and Pharmaceutical Composition

The present invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the present invention will be administered in a therapeutically effective amount by any of the accepted modes of administration for agents that serve similar utilities. Suitable dosage ranges are typically 1–500 mg daily, preferably 1–100 mg daily, and most preferably 1–30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

In general, compounds of the present invention will be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the present invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the present invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to a skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in Remington: The Science and Practice of pharmacy 1995, edited by E. W. Martin, Mack Publishing Company, 19th edition, Easton, Pa. Representative pharmaceutical formulations containing a compound of the present invention are described in Examples 6–12.

EXAMPLES

The following preparations and examples are given to enable those skilled in the art to more clearly understand and to practice the present invention. They should not be considered as limiting the scope of the invention, but merely as being illustrative and representative thereof.

Example 1

3-Benzenesulfonyl-7-(2-piyrrolidin-1-yl-ethoxy)-1H-indole Hydrochloride

This example illustrates a method for producing 3-benzenesulfonyl-7-(2-pyrrolidin-1-yl-ethoxy)-1H-indole hydrochloride and other substituted indole compounds in accordance with the invention using the synthetic procedure outlined below in Scheme C.

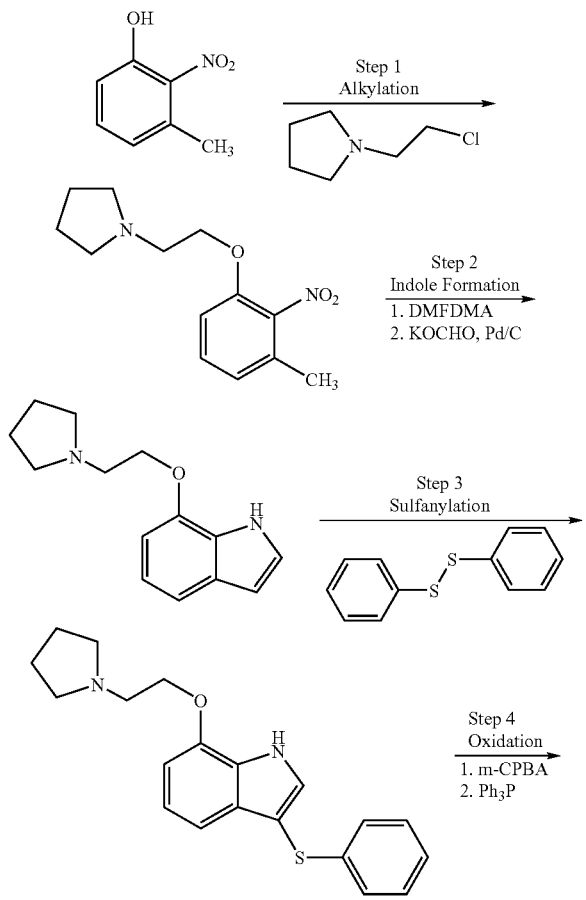

-continued

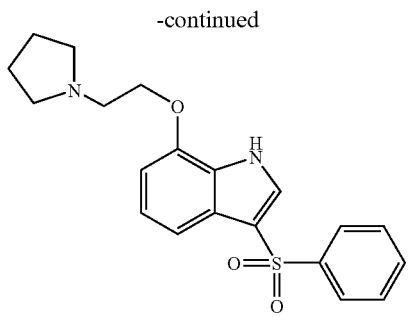

Step 1

1-[2-(3-Methyl-2-nitrophenoxy)-ethyl]-pyrrolidine

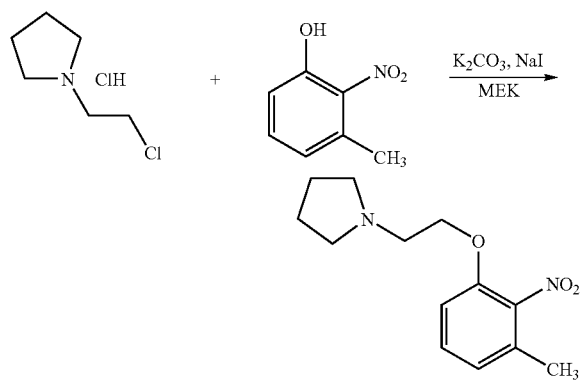

Potassium carbonate (34.9 g., 252 mmol) and sodium iodide (1.0 g., 6.5 mmol) were added to a solution of 3-methyl-2-nitrophenol (10 g., 65.3 mmol). With stirring, 1-(2-chloroethyl)-pyrrolidine hydrochloride (16.65 g., 98 mmol) was added portion-wise to the solution. The reaction mixture was refluxed for 15 hours, at which time 1-(2-chloroethyl)-pyrrolidine hydrochloride (8.5 g., 50 mmol) and potassium carbonate (18 g., 130 mmol) were added. After an additional hour of reflux, the reaction mixture was allowed to cool to room temperature and was washed with sequentially with water (1×100 mL) and brine (1×100 mL.) The combined organic fractions spontaneously crystallized, and the solid was purified by flash chromatography (5% MeOH in CH$_2$Cl$_2$) to give 1-[2-(3-Methyl-2-nitrophenoxy)-ethyl]-pyrrolidine (10.291 g., 69%). MS: 251 (M+H)$^+$ Also prepared in a similar fashion, using N-(2-chloro-ethy)-dimethylamine hydrochloride as an electrophile rather than 1-(2-chloroethyl)-pyrrolidine hydrochloride, was the compound: Dimethyl-[2-(3-methyl-2-nitro-phenoxy)-ethyl]-amine (72%), MS: 225 (M+H)$^+$ Step 2

7-(2-pyrrolidin-1-yl-ethoxy)-1H-indole

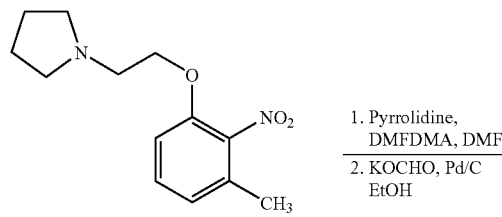

-continued

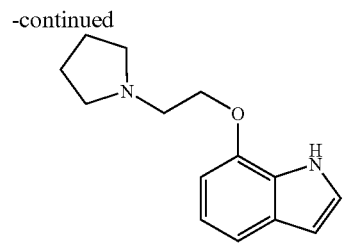

A 100 mL flask equipped with magnetic stirrer and reflux condenser was charged with 1-[2-(3-methyl-2-nitrophe-noxy)-ethyl]-pyrrolidine (5.8 g., 23 mmol) from Step 1 and 50 mL dimethylformamide. To this solution was added pyrrolidine (5.0 g., 70 mmol) and dimethylformamide dim-ethylacetal (8.3 g., 70 mmol.). With stirring, the solution was refluxed at 140° C. for 20 hours. The reaction mixture was concentrated by heating at 100° C. under 500 millitorr pressure for 5 hours, giving a crude brown solid which was dissolved in 50 mL ethanol. To this solution was added 100 mg of 5% Pd on charcoal and potassium formate (10.73 g., 128 mmol.). The reaction mixture was refluxed ad 85° C. for 1 hour and concentrated in vacuo. The crude residue was purified by flash chromatography (5% MeOH in CH$_2$Cl$_2$) to give 4.53 g. of 7-(2-pyrrolidin-1-yl-ethoxy)-1H-indole as a viscous oil (74%), MS: 231 (M+H)$^+$ The following compound was prepared in a similar fashion, starting with dimethyl-[2-(3-methyl-2-nitro-phenoxy)-ethyl]-amine rather than 1-[2-(3-methyl-2-nitrophenoxy)-ethyl]-pyrrolidine: [2-(1H-indol-7-yloxy)-ethyl]-dimethyl-amine (69%), MS: 205 (M+H)$^+$ Step 3

3-Phenylsulfanyl-7-(2-pyrrolidin-1-yl-ethoxy)-1H-indole

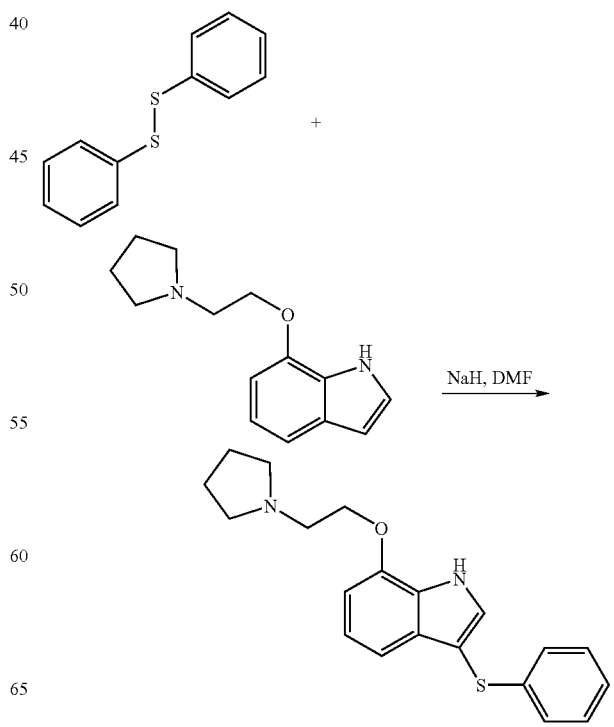

To a solution of 7-(2-pyrrolidin-1-yl-ethoxy)-1H-indole (0.610 g., 2.7 mmol) in 15 mL anhydrous dimethylformamide was added sodium hydride (0.140 g. of a 60% suspension in mineral oil, 3.5 mmol) portion-wise. The solution was stirred with a magnetic stirrer at room temperature for 20 minutes, at which time the initial off-gassing ended. Phenyl disulfide (0.654 g., 3 mmol) was added in one portion and the reaction mixture was stirred at room temperature for 8 hours. The reaction mixture was partitioned between water (50 mL) and ethyl acetate (50 mL). The aqueous layer was extracted with ethyl acetate (2×25 mL) and the combined organic fractions were washed with water (2×25 mL) and brine (2×25 mL). After drying over $MgSO_4$, the organic fraction was concentrated in vacuo and the resulting brown residue was purified by flash chromatography (10:1:0.1, $CH_2Cl_2$:MeOH:$NH_4OH$) to give 0.653 g. 3-phenylsulfanyl-7-(2-pyrrolidin-1-yl-ethoxy)-1H-indole as a viscous brown oil (72%) MS: 339 $(M+H)^+$ The following compounds were prepared in a similar fashion using various aryl disulfides that are either commercially available or known in the literature:

3-(3-Chloro-phenylsulfanyl)-7-(2-pyrrolidin-1-yl-ethoxy)-1H-indole, $^1$H NMR (CDCl$_3$, 300 MHz) δ: 1.86 (p, 4H, J=3.6), 2.68 (m, 4H), 2.97 (t, 2H, J=5.3), 4.26 (t, 2H, J=5.4), 6.71 (dd, 1H, J=6.97, J'=0.6), 6.92–7.08 (m, 5H), 7.20 (dd, 1H, J=7.35, J'=0.8), 7.42 (s, 1H);

3-(4-Chloro-phenylsulfanyl)-7-(2-pyrrolidin-1-yl-ethoxy)-1H-indole, $^1$H NMR (CDCl$_3$, 300 MHz) δ: 1.83 (p, 4H, J=3.4), 2.66 (m, 4H), 2.95 (t, 2H, J=5.4), 4.24 (t, 2H, J=5.4), 6.7 (d, 1H, J=7.7), 6.93–7.09 (m, 5H), 7.17 (d, 1H J=7.9), 7.83 (s, 1H);

3-(2,3-Dichloro-phenylsulfanyl)-7-(2-pyrrolidin-1-yl-ethoxy)-1H-indole, $^1$H NMR (CDCl$_3$, 300 MHz) δ: 1.86 (p, 4H, J=3.3), 2.68 (m, 4H), 2.97 (t, 2H, J=5.5), 4.27 (t, 2H, J=5.5), 6.59 (dd, 1H, J=6.5, J'=1.4), 6.73 (d, 1H, J=7.4), 6.80 (t, 1H, J=7.9), 7.04 (t, 1H, J=7.9), 7.10 (dd, 1H, J=7.9, J'=1.3), 7.18 (d, 1H, J=7.9), 7.88 (s, 1H);

3-(2-Chloro-phenylsulfanyl)-7-(2-pyrrolidin-1-yl-ethoxy)-1H-indole, $^1$H NMR (CDCl$_3$, 300 MHz) δ: 1.88 (p, 4H, J=3.6), 2.70 (m, 4H), 2.98 (t, 2H, J=5.4), 4.28 (t, 2H, J=5.4), 6.65 (dd, 1H, J=7.5, J'=1.9), 6.73 (d, 1H, J=7.7), 6.89–7.00 (m, 2H), 7.04 (t, 1H, J=7.9), 7.21 (dd, 1H, J=8.1, J'=0.7), 7.31 (dd, 1H, J=7.4, J'=1.9), 7.46 (s, 1H);

3-(3,4-Dichloro-phenylsulfanyl)-7-(2-pyrrolidin-1-yl-ethoxy)-1H-indole, $^1$H NMR (CDCl$_3$, 300 MHz) δ: 1.83 (q, 4H, J=3.3), 2.68 (m, 4H), 2.96 (t, 2H, J=5.4), 4.26 (t, 2H, J=5.4), 6.72 (d, 1H, J=7.7), 6.83 (dd, 1H, J=8.5, J'=2.3), 7.03 (t, 1H, J=7.8), 7.10–7.18 (m, 3H), 7.84 (s, 1H);

3-(2-Fluoro-phenylsulfanyl)-7-(2-pyrrolidin-1-yl-ethoxy)-1H-indole, $^1$H NMR (CDCl$_3$, 300 MHz) δ: 1.85 (q, 4H, J=3.3), 2.67 (m, 4H), 2.96 (t, 2H, J=5.4), 4.25 (m, 2H), 6.72 (m, 2H), 6.81 (dd, 1H, J=7.9, J'=0.6), 6.97–7.01 (m, 2H), 7.04 (d, 1H, J=7.7), 7.22 (dd, 1H, J=7.9, J'=0.9), 7.40 (s, 1H);

3-(3-Fluoro-phenylsulfanyl)-7-(2-pyrrolidin-1-yl-ethoxy)-1H-indole, $^1$H NMR (CDCl$_3$, 300 MHz) δ: 1.86 (q, 4H, J=3.3), 2.68 (m, 4H), 2.97 (t, 2H, J=5.3), 4.26 (m, 2H), 6.67–6.73 (m, 3H), 6.87 (d, 1H, J=7.53), 7.04 (t, 1H, J=7.8), 7.05–7.13 (m, 1H), 7.22 (t, 1H, J=7.9), 7.40 (s, 1H);

3-(3-Methoxy-phenylsulfanyl)-7-(2-pyrrolidin-1-yl-ethoxy)-1H-indole, $^1$H NMR (CDCl$_3$, 300 MHz) δ: 1.84 (q, 4H, J=3.3), 2.68 (m, 4H), 2.96 (t, 2H, J=5.5), 3.95 (s, 3H), 4.26 (t, 2H, J=5.5), 6.58–6.68 (m, 2H), 6.72 (dd, 1H, J=7.7, J'=0.8), 6.82 (dd, 1H, J=8.0, J'=0.9), 6.98–7.05 (m, 2H), 7.23 (dd, 1H, J=8.0, J'=0.8), 7.88 (d, 1H, J=1.7); and 3-(2-Methoxy-phenylsulfanyl)-7-(2-pyrrolidin-1-yl-ethoxy)-1H-indole, $^1$H NMR (CDCl$_3$, 300 MHz) δ: 1.85 (q, 4H, J=3.3), 2.68 (m, 4H), 2.96 (t, 2H, J=5.5), 3.9 (s, 3H), 4.26 (t, 2H, J=5.5), 6.62 (m, 1H), 6.72 (m, 1H), 6.87 (m, 1H), 6.85–7.01 (m, 3H), 7.20 (m, 1H), 7.88 (s, 1H).

The following compounds were prepared in a similar fashion starting with [2-(1H-indol-7-yloxy)-ethyl]-dimethyl-amine and using various aryl disulfides that are either commercially available or known in the literature:

[2-(3-Benzenesulfanyl-1H-indol-7-yloxy)-ethyl]-dimethyl-amine, $^1$H NMR (CDCl$_3$, 300 MHz) δ: 2.36 (s, 6H), 2.77 (t, 2H, J=5.3), 4.22 (t, 2H, J=5.3), 6.71 (dd, 1H, J=7.5, J'=0.7), 6.97–7.15 (m, 6H), 7.23 (d, 1H, J=7.8), 7.36 (d, 1H, J=2.5)

{2-[3-(2-Methoxy-phenylsulfanyl)-1H-indol-7-yloxy]-ethyl}-dimethyl-amine, $^1$H NMR (CDCl$_3$, 300 MHz) δ: 2.34 (s, 6H), 2.77 (t, 2H, J=5.3), 3.65 (s, 3H), 4.20 (t, 2H, J=5.3), 6.57 (m, 1H), 6.64–6.69 (m, 3H), 6.99–7.07 (m, 2H), 7.21 (d, 1H, J=7.4)

{2-[3-(2-Fluoro-phenylsulfanyl)-1H-indol-7-yloxy]-ethyl}-dimethyl-amine, $^1$H NMR (CDCl$_3$, 300 MHz) δ: 2.34 (s, 6H), 2.79 (t, 2H, J=5.4), 4.22 (t, 2H, J=5.4), 6.72 (m, 2H), 6.81 (dd, 1 H, J=7.5, J'=0.6), 6.99–7.02 (m, 2H), 7.03 (d, 1H, J=7.4), 7.22 (dd, 1H, J=7.6, J'=0.9), 7.40 (s, 1H)

Step 4

3-Benzenesulfonyl-7-(2-pyrrolidin-1-yl-ethoxy)-1H-indole Hydrochloride

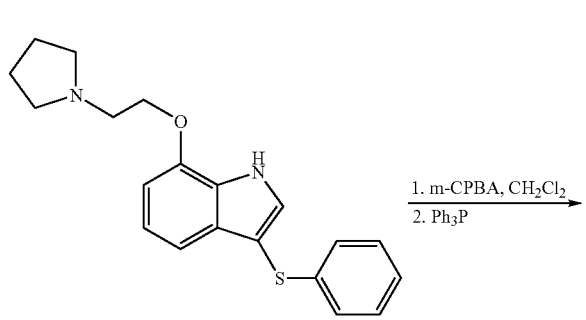

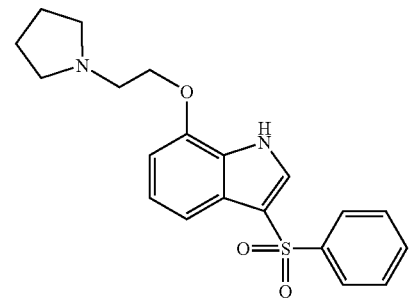

A solution of 3-phenylsulfanyl-7-(2-pyrrolidin-1-yl-ethoxy)-1H-indole (0.527 g., 1.6 mmol) in 30 mL $CH_2Cl_2$ was prepared in a 50 mL roundbottom flask equipped with a magnetic stirrer. The solution was stirred, cooled to 0° C. and meta-chloroperoxybenzoic acid (1.15 g., 5.2 mmol) was added portion-wise. The solution was allowed to warm to room temperature and stirring was continued for 6 hours. Triphenyl phosphine (1.36 g., 5.2 mmol) was then added and the solution was stirred for 48 hours. The reaction mixture was washed with water (1×25 mL), 2M aqueous potassium carbonate solution (1×25 mL) and brine (1×25 mL). The combined organic fractions were dried over MgSO₄ and concentrated in vacuo. The residue was purified by flash chromatography (5% MeOH in CH₂Cl₂) and recrystallized from 2 M ethanolic hydrogen chloride to give 0.180 g. of 3-benzenesulfonyl-7-(2-pyrrolidin-1-yl-ethoxy)-1H-indole hydrochloride as a light pink crystal. MS: 371 (M+H)⁺, mp=265.1–273.4° C.

The following compounds were prepared in a similar fashion starting with the appropriate sulfide:

3-(3-Chloro-phenylsulfonyl)-7-(2-pyrrolidin-1-yl-ethoxy)-1H-indole hydrochloride, MS: 405 (M+H)⁺, mp=257–260.1° C.;

3-(4-Chloro-phenylsulfonyl)-7-(2-pyrrolidin-1-yl-ethoxy)-1H-indole hydrochloride, MS: 405 (M+H)⁺;

3-(2,3-Dichloro-phenylsulfonyl)-7-(2-pyrrolidin-1-yl-ethoxy)-1H-indole hydrochloride, MS: 439 (M+H)⁺, mp=260–262.4° C.;

3-(2-Chloro-phenylsulfonyl)-7-(2-pyrrolidin-1-yl-ethoxy)-1H-indole hydrochloride, MS: 405 (M+H)⁺;

3-(3,4-Dichloro-phenylsulfonyl)-7-(2-pyrrolidin-1-yl-ethoxy)-1H-indole hydrochloride, MS: 439; (M+H)⁺, mp=257.8–262.9° C.;

3-(2-Fluoro-phenylsulfonyl)-7-(2-pyrrolidin-1-yl-ethoxy)-1H-indole hydrochloride, MS: 389 (M+H)⁺ mp=266.7–269.7° C.;

3-(3-Fluoro-phenylsulfonyl)-7-(2-pyrrolidin-1-yl-ethoxy)-1H-indole hydrochloride, MS: 389 (M+H)⁺, mp=275–279.1° C.;

3-(3-Methoxy-phenylsulfonyl)-7-(2-pyrrolidin-1-yl-ethoxy)-1H-indole hydrochloride, MS: 401 (M+H)⁺;

3-(2-Methoxy-phenylsulfonyl)-7-(2-pyrrolidin-1-yl-ethoxy)-1H-indole hydrochloride, MS: 401 (M+H)⁺, mp=212–213.9° C.;

[2-(3-Benzenesulfonyl-1H-indol-7-yloxy)-ethyl]-dimethyl-amine hydrochloride, MS: 344 (M+H)⁺, mp=248.5–250.1° C.;

{2-[3-(2-Methoxy-phenylsulfonyl)-1H-indol-7-yloxy]-ethyl}-dimethyl-amine hydrochloride, MS: 375 (M+H)⁺, mp=242.9–245.3° C.;

{2-[3-(2-Fluoro-phenylsulfonyl)-1H-indol-7-yloxy]-ethyl}-dimethyl-amine, MS: 363 (M+H)⁺, mp=250–253.8° C.; and 3-(2,5-Dichloro-benzenesulfonyl)-7-(2-pyrrolidin-1-yl-ethoxy)-1H-indole. MS: 440 (M+H)⁺.

Example 2

[2-(3-benzenesulfonyl-1H-indol-7-yloxy)-ethyl]-methyl-amine Hydrochloride

This example illustrates a method for producing [2-(3-benzenesulfonyl-1H-indol-7-yloxy)-ethyl]-methyl-amine hydrochloride and other substituted indole compounds in accordance with the invention using the synthetic procedure outlined below in Scheme D.

SCHEME D

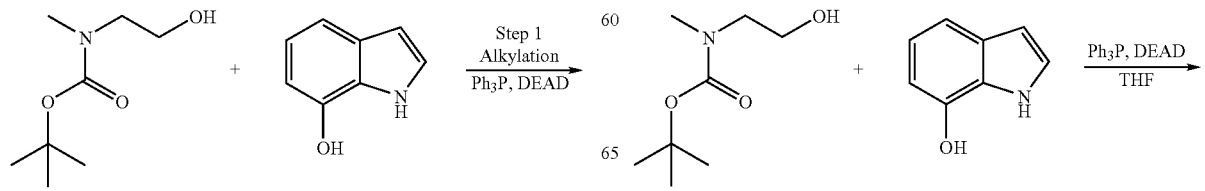

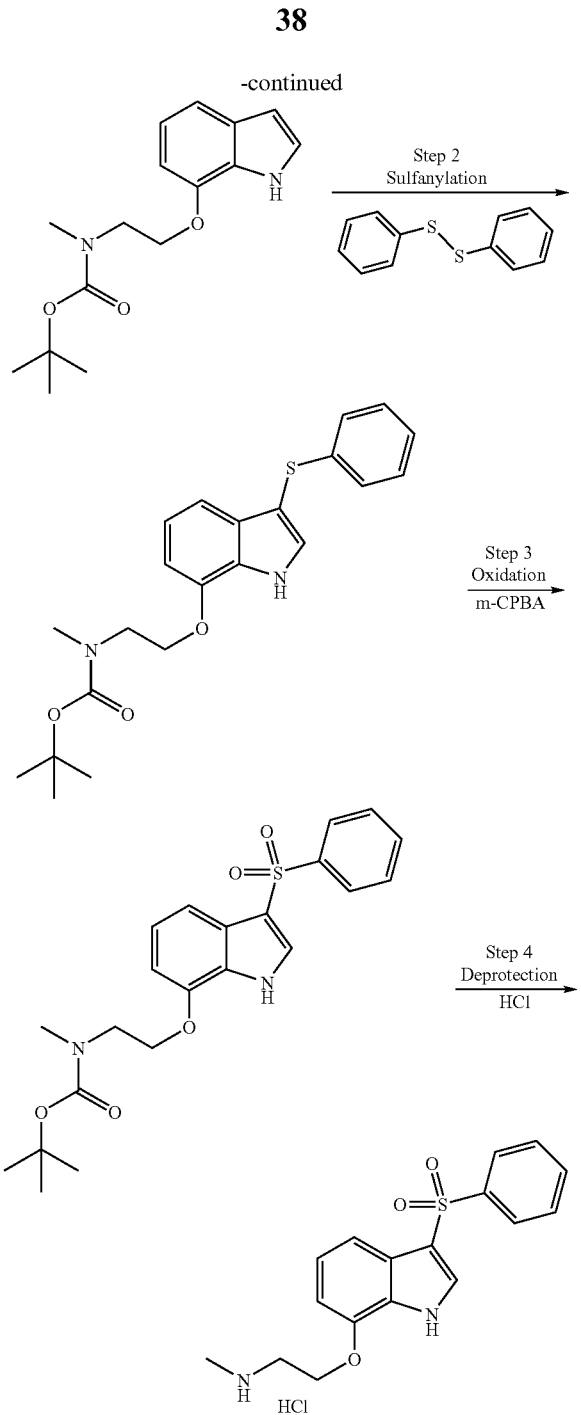

Step 1

[2-(1H-indol-7-yloxy)-ethyl]-methyl-carbamic Acid Tert-butyl Ester

-continued

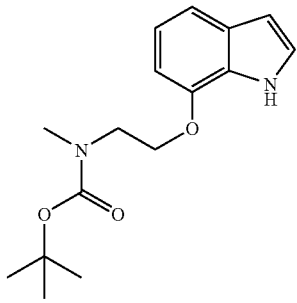

A 50 mL flask equipped with magnetic stirrer was charged with 7-hydroxy-1H-indole (0.450 g., 3.4 mmol), (2-hydroxy-ethyl)-methyl-carbamic acid tert-butyl ester (0.945 g., 5.1 mmol) and triphenyl phosphine (1.43 g., 5.4 mmol). To this was added 10 mL anhydrous THF and the system was purged with $N_2$. Diethylazodicaboxylate (0.948 g., 5.4 mmol) was added as a solution in 5 mL anhydrous THF. The reaction mixture was stirred for 48 hours, at which time the solvent was removed in vacuo to give a red oil. This residue was purified by flash chromatography (95:5 hexane:EtOAc to 75:25 hexane:EtOAc over 35 minutes) to give 0.458 g. of [2-(1H-indol-7-yloxy)-ethyl]-methyl-carbamic acid tert-butyl ester as a pink solid: MS: 289 (M-H)$^-$.

The following compounds were prepared in a similar fashion using 7-hydroxy-1H-indole and the appropriate alcohols:
(S)-2-(1H-Indol-7-yloxymethyl)-pyrrolidine-1-carboxylic acid tert-butyl ester $^1$H NMR (CDCl$_3$, 300 MHz) δ: 1.48 (s, 9H), 2.02 (m, 4H), 3.41 (m, 2H), 4.01 (m, 1H), 4.26 (m, 2H), 6.51 (m, 1H), 6.69 (d, 1H, J=7.7), 6.99 (t, 1H, J=7.8), 7.16 (t, 1H, J=2.6), 7.25 (d, 1H J=7.8); and
4-(1H-Indol-7-yloxy)-piperidine-1-carboxylic acid tert-butyl ester, MS: 315 (M-H)$^-$.

Step 2

[2-(3-benzenesulfanyl-1H-indol-7-yloxy)-ethyl]-methyl-carbamic Acid tert-butyl Ester

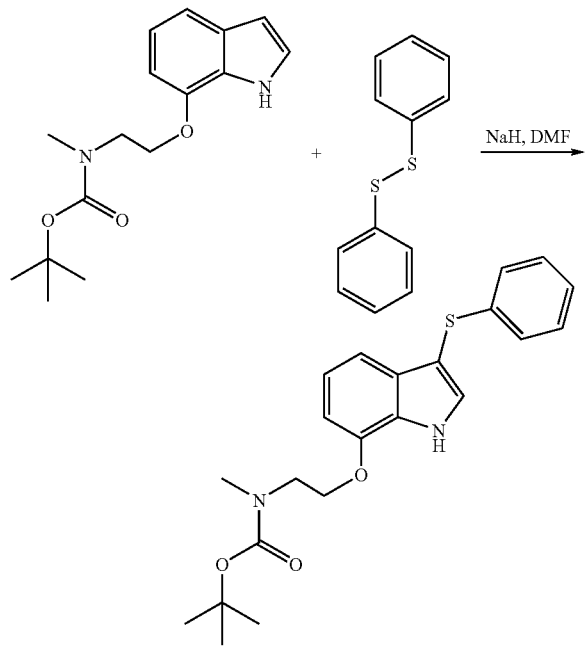

[2-(1H-Indol-7-yloxy)-ethyl]-methyl-carbamic acid tert-butyl ester (0.174 g., 0.6 mmol) from Step 1 was dissolved in 5 mL anhydrous dimethylformamide in a dry 50 mL flask equipped with magnetic stirrer. This solution was treated with sodium hydride (0.026 g. of a 60% suspension in mineral oil, 0.66 mmol) and stirred under $N_2$ for 20 minutes. With stirring, phenyl disulfide (0.156 g., 0.72 mmol) was added in one portion. Stirring is continued for 72 hours, at which time the reaction mixture was washed with water (1×45 mL) and brine (1×45 mL.) The organic fraction was dried over MgSO$_4$ and concentrated in vacuo and the resulting residue was purified by flash chromatography (95:5 hexane:EtOAc to 75:25 hexane:EtOAc over 35 minutes) to give 0.255 g. [2-(3-benzenesulfonyl-1H-indol-7-yloxy)-ethyl]-methyl-carbamic acid tert-butyl ester as a red oil. $^1$H NMR (CDCl$_3$, 300 MHz) δ: 1.47 (s, 9H), 2.99 (s, 3H), 3.69 (t, 2H, J=5.4), 4.28 (t, 2H, J=5.5), 6.70 (d, 1H, J=7.7), 6.73–6.76 (m, 3H), 6.96–7.08 (m, 3H), 7.22 (d, 1H, J=7.8), 7.46 (d, 1H, J=2.6).

The following compounds were prepared in a similar fashion starting the appropriate indole ether (see Scheme D, Step 1 above) and using various aryl disulfides, which are all either commercially available or known in the literature:
{2-[3-(2-fluoro-benzenesulfanyl)-1H-indol-7-yloxy]-ethyl}-methyl-carbamic acid tert-butyl ester, MS: 415 (M-H)$^-$;
(S)-2-[3-(2-fluoro-benzenesulfanyl)-1H-Indol-7-yloxymethyl]-pyrrolidine-1-carboxylic acid tert -butyl ester, MS: 443 (M+H)$^+$; and 4-(3-benzenesulfanyl-1H-indol-7-yloxy)-piperidine-1-carboxylic acid tert-butyl ester, MS: 423 (M-H)$^-$.

Step 3

[2-(3-benzenesulfonyl-1H-indol-7-yloxy)-ethyl]-methyl-carbamic Acid Tert-butyl Ester

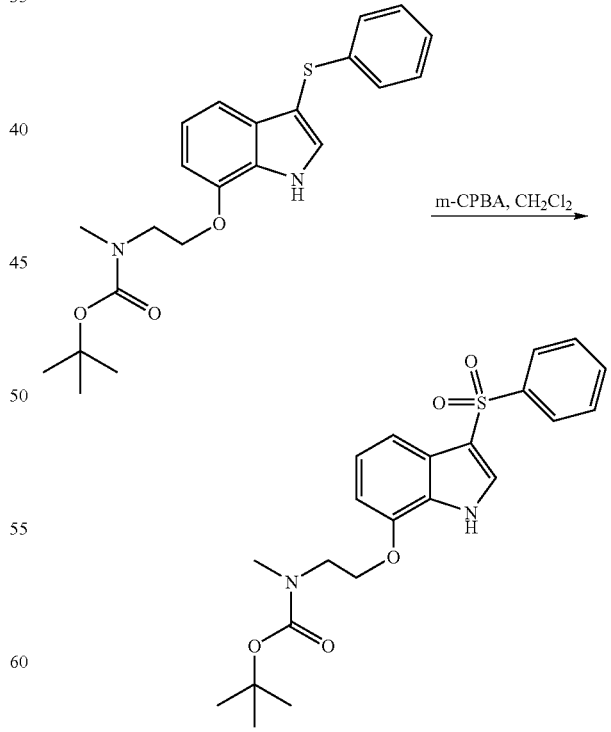

A 25 mL flask equipped with a magnetic stirrer was charged with a solution of [2-(3-benzenesulfanyl-1H-indol-7-yloxy)-ethyl]-methyl-carbamic acid tert-butyl ester (0.255 g., 0.6 mmol) in 15 mL of dichloromethane. This solution was cooled to 0° C. and meta-chloroperoxybenzoic acid was added portion-wise over 10 minutes. The reaction mixture was allowed to warm to room temperature and stirring was continued for 2 hours. The reaction mixture was washed with 1 M sodium hydroxide solution (2×45 mL) and water (1×45 mL.) The organic fractions were dried over MgSO$_4$ and concentrated in vacuo. The resulting residue was purified by flash chromatography (85:15 hexanes:EtOAc to 65:35 hexanes:EtOAc over 30 minutes) to give 0.207 g. of [2-(3-benzenesulfonyl-1H-indol-7-yloxy)-ethyl]-methyl-carbamic acid tert-butyl ester as white crystals. $^1$H NMR (CDCl$_3$, 300 MHz) δ: 1.45 (s, 9H), 2.93 (s, 3H), 3.63 (t, 2H, J=5.3), 4.32 (t, 2H, J=5.3), 6.70 (d, 1H, J=7.7), 7.13 (t, 1H, J=8.0), 7.40–7.48 (m, 3H), 7.51 (d, 1H, J=8.0), 7.85 (d, 1H, J=3.0), 8.01 (m, 2H).

The following compounds were prepared in a similar fashion starting with the appropriate sulfide:

{2-[3-(2-fluoro-benzenesulfonyl)-1H-indol-7-yloxy]-ethyl}-methyl-carbamic acid tert-butyl ester, MS: 447 (M–H)$^-$;

(S)-2-[3-(2-fluoro-benzenesulfonyl)-1H-Indol-7-yloxymethyl]-pyrrolidine-1-carboxylic acid tert-butyl ester. $^1$H NMR (CDCl$_3$, 300 MHz) δ: 1.47 (s, 9H), 1.90 (m, 4H), 3.89 (m, 2H), 4.00 (m, 1H), 4.24 (m, 2H), 6.71 (m, 1H), 7.02 (t, 2H, J=9.6), 7.26 (td, 1H, J=7.7, J'=0.9), 7.34–7.54 (m, 2H), 8.01 (m, 1H), 8.16 (td, 1H. J=7.7, J'=1.9); and 4-(3-benzenesulfonyl-1H-indol-7-yloxy)-piperidine-1-carboxylic acid tert-butyl ester, $^1$H NMR (CDCl$_3$, 300 MHz) δ: 1.47 (s, 9H), 1.77 (m, 2H), 2.00 (m, 2H), 3.28 (m, 2H), 3.77 (m, 2H), 4.63 (m, 1H), 6.72 (d, 1H, J=7.91), 7.15 (t, 1H, J=8.0), 7.48 (m, 4H), 7.88 (d, 1H, J=3.0), 8.03 (m, 2H).

Step 4

[2-(3-benzenesulfonyl-1H-indol-7-yloxy)-ethyl]-methyl-amine Hydrochloride

[2-(3-Benzenesulfonyl-1H-indol-7-yloxy)-ethyl]-methyl-amine (0.207 g., 0.5 mmol) from Step 3 was dissolved in 4 mL ethanol. To this solution was added 2 M ethanolic hydrochloric acid solution (3 mL.) The reaction mixture was heated at 100° C. for 20 minutes, at which time a crystalline solid formed. The solution was allowed to cool to room temperature and 0.165 g. of [2-(3-benzenesulfonyl-1H-indol-7-yloxy)-ethyl]-methyl-amine hydrochloride was collected as a white powder. MS: 331 (M+H)$^+$, mp=270.4–276.1° C.

Using the same deprotection procedure, the following compounds were obtained:

{2-[3-(2-Fluoro-benzenesulfonyl)-1H-indol-7-yloxy]-ethyl}-methyl-amine hydrochloride, MS: 349 (M+H)$^+$, mp=225.0–227.3° C.;

(S)-3-(2-Fluoro-benzenesulfonyl)-7-(pyrrolidin-2-ylmethoxy)-1H-indole hydrochloride, MS: 375 (M+H)$^+$, mp=255.6–263.7° C.; and 3-Benzenesulfonyl-7-(piperidin-4-yloxy)-1H-indole hydrochloride, MS: 357 (M+H)$^+$, mp=157.5–164.5° C.

Example 3

[2-(3-Benzenesulfonyl-1-methyl-1H-indol-7-yloxy)-ethyl]-methyl-amine Hydrochloride This example illustrates a method for producing [2-(3-Benzenesulfonyl-1-methyl-1H-indol-7-yloxy)-ethyl]-methyl-amine hydrochloride in accordance with the invention using the synthetic procedure outlined below in Scheme E.

SCHEME E

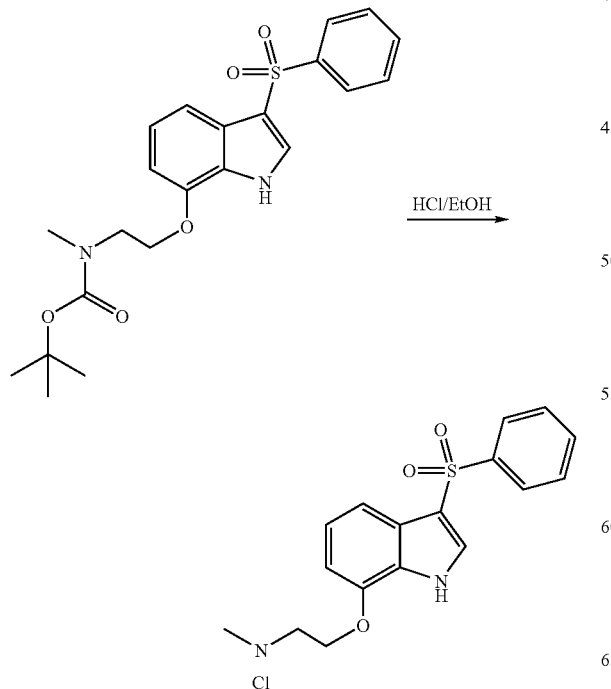

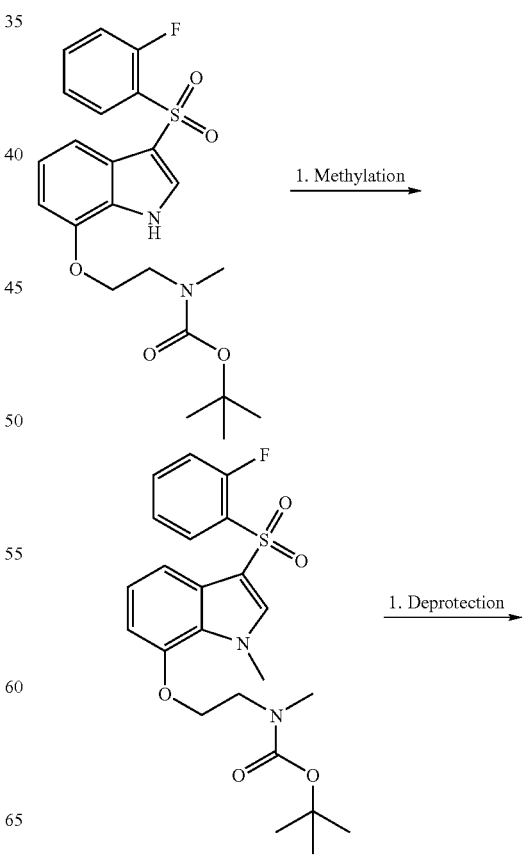

-continued

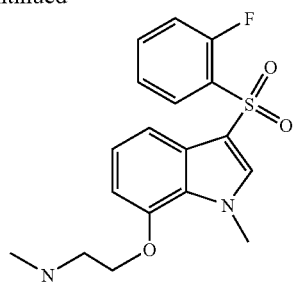

Step 1

{2-[3-(2-fluoro-benzenesulfonyl)-1-methyl-1H-indol-7-yloxy]-ethyl}-methyl-carbamic Acid Tert-butyl Ester

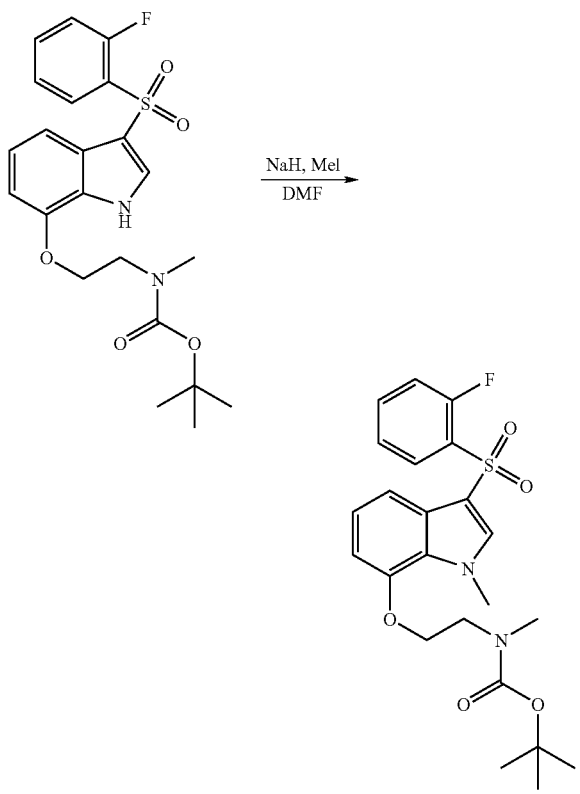

A dry 25 mL flask equipped with a magnetic stirrer was charged with {2-[3-(2-fluoro-benzenesulfonyl)-1H-indol-7-yloxy]-ethyl}-methyl-carbamic acid tert-butyl ester (0.116 g., 0.258 mmol) and dimethylformamide (5 mL.) This solution was treated with sodium hydride (0.011 g. of 60% suspension in mineral oil, 0.284 mmol) and allowed to stir for 10 minutes under $N_2$. Methyl iodide was then added via syringe in one portion. After 18 hours stirring at ambient temperature, the reaction mixture was extracted into 45 mL ethyl acetate and washed with water (2×45 mL). The organic fraction was dried over $MgSO_4$ and concentrated in vacuo. The residue was purified by flash chromatography (85:15 hexanes:EtOAc to 70:30 hexanes:EtOAc) to give 45 mg of {2-[3-(2-fluoro-benzenesulfonyl)-1-methyl-1H-indol-7-yloxy]-ethyl}-methyl -carbamic acid tert-butyl ester as a clear oil: $^1$H NMR (CDCl$_3$, 300 MHz) δ: 1.45 (s, 9H), 2.94 (s, 3H), 3.71 (m, 2H), 4.09 (s, 3H), 4.19 (m, 2H), 6.67 (d, 1H, J=7.7), 7.04 (m, 1H), 7.08 (t, 1H, J=8.0), 7.27 (td, 1H, J=7.6, J'=1.13), 7.44 (d, 1H, J=7.6), 7.49 (m, 1H), 7.74 (d, 1H, J=1.3), 8.15 (td, 1H, J=7.6, J'=1.8).

Step 2

2-(3-Benzenesulfonyl-1-methyl-1H-indol-7-yloxy)-ethyl]-methyl-amine Hydrochloride

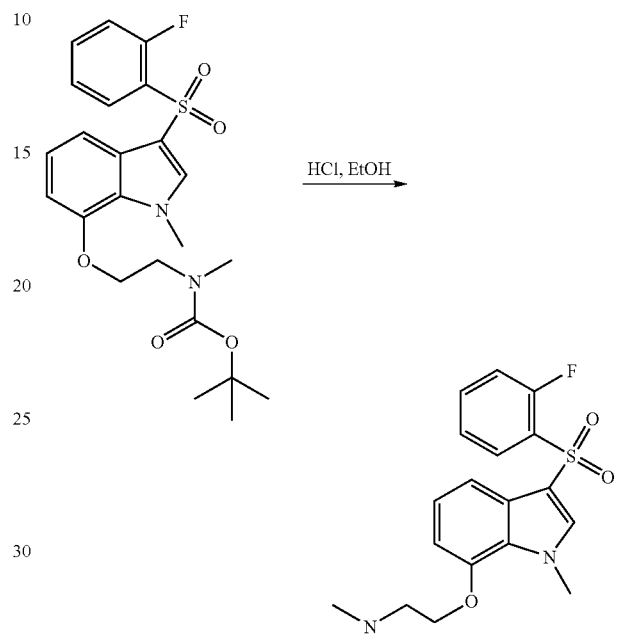

To a solution of {2-[3-(2-fluoro-benzenesulfonyl)-1-methyl-1H-indol-7-yloxy]-ethyl}-methyl-carbamic acid tert-butyl ester (0.045 mg, 0.09 mmol) in 3 mL EtOH was added 1 mL of 2M ethanolic hydrogen chloride. The reaction mixture was heated at 100° C. for 20 minutes at which time the solvent was removed in vacuo to give a clear residue which was recrystallized from EtOH to give 0.028 g. [2-(3-benzenesulfonyl-1-methyl-1H-indol-7-yloxy)-ethyl]-methyl-amine hydrochloride as a white powder. MS: 363 (M+H)$^+$, mp=225.0–227.3° C.

Example 4

[2-(2-benzenesulfonyl-1H-indol-4-yloxy)-ethyl]-methyl-amine Hydrochloride

This example illustrates a method for producing [2-(2-benzenesulfonyl-1H-indol-4-yloxy)-ethyl]-methyl-amine hydrochloride and other substituted indole compounds in accordance with the invention using the synthetic procedure outlined below in Scheme F.

SCHEME F

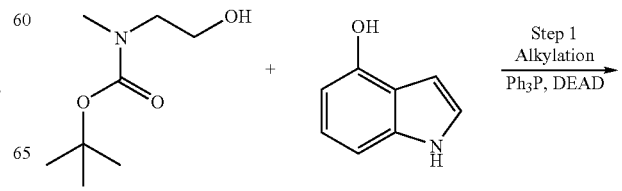

-continued

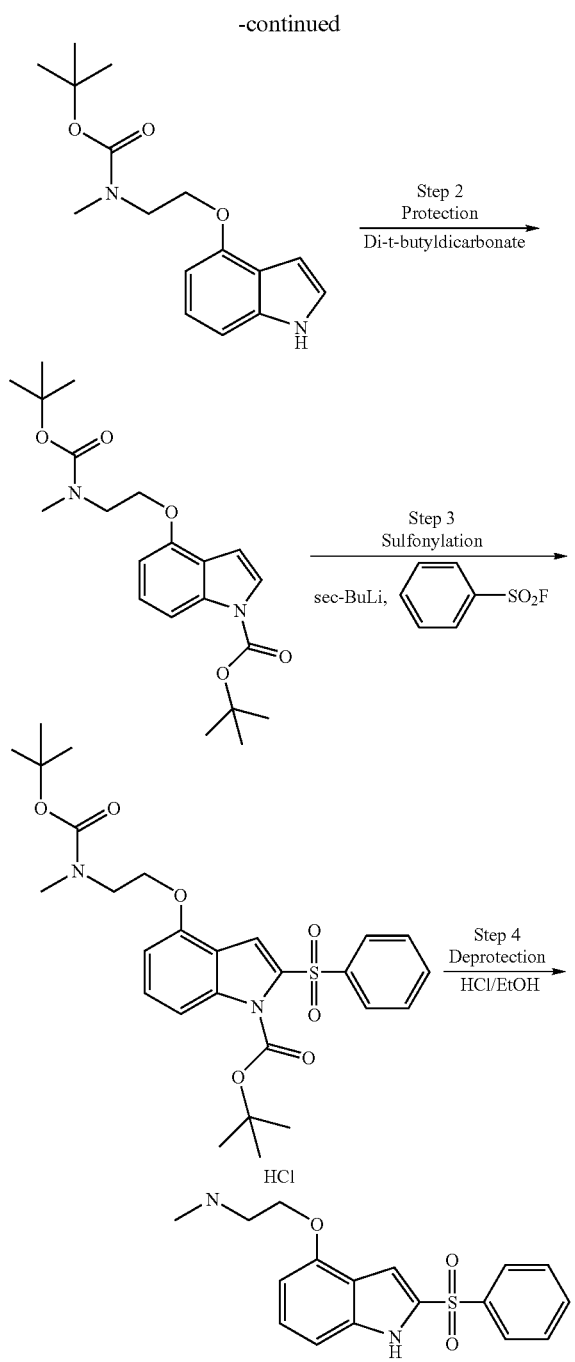

In this step, (2-hydroxy-ethyl)-methyl-carbamic acid tert-butyl ester was prepared as described in *J. Med Chem.* (1999), 42(11), 2007–2020.

A 500 mL roundbottom flask equipped with a magnetic stirrer was charged with 4-hydroxy-1H-indole (11.11 g., 83 mmol) and 100 mL anhydrous THF. To this was added (2-hydroxy-ethyl)-methyl-carbamic acid tert-butyl ester (16.1 g., 91 mmol) and the solution was cooled to 0° C. Triphenylphosphine (35.04 g., 133 mmol) was added portion-wise and the solution was allowed to warm to ambient temperature. The system was purged with $N_2$ and diethyla-zodicarboxylate (23.27 g., 133 mmol) was added via syringe. The solution was allowed to stir at ambient temperature for 72 hours. The reaction mixture was then washed with water (1×50 mL) and 2 M aqueous sodium hydroxide solution (2×50 mL), dried over $MgSO_4$ and concentrated in vacuo. The residue was dissolved in diethyl ether and solid triphenylphosphine oxide was precipitated with 5 mL hexanes. The crystalline material was filtered and the filtrate was concentrated in vacuo and the resulting oil was purified by flash chromatography (Pure hexanes-80:20 hexanes:EtOAc over 30 minutes) to give 18.23 g. [2-(1H-indol-4-yloxy)-ethyl]-methyl-carbamic acid tert-butyl ester as a yellowish oil. MS: 288 (M–H)⁻.

In a similar manner, using 3-hydroxymethyl-azetidine-1-carboxylic acid tert-butyl ester in place of (2-hydroxy-ethyl)-methyl-carbamic acid tert-butyl ester, 3-(1H-Indol-4-yloxymethyl)-azetidine-1-carboxylic acid tert-butyl ester was prepared, (25%), (M–H)⁻=301.

Step 2

4-[2-(tert-butoxycarbonyl-methyl-amino)-ethoxy]-indole-1-carboxylic Acid tert-butyl Ester

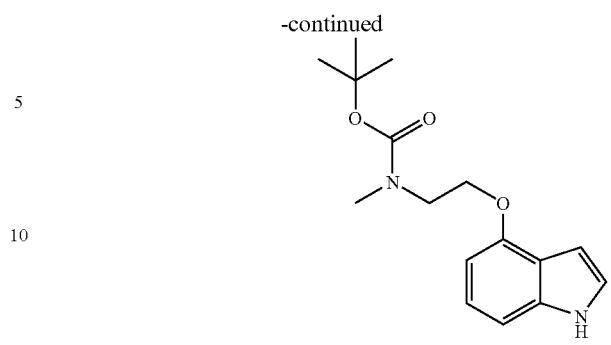

Step 1

[2-(1H-indol-4-yloxy)-ethyl]-methyl-carbamic Acid Tert-butyl Ester

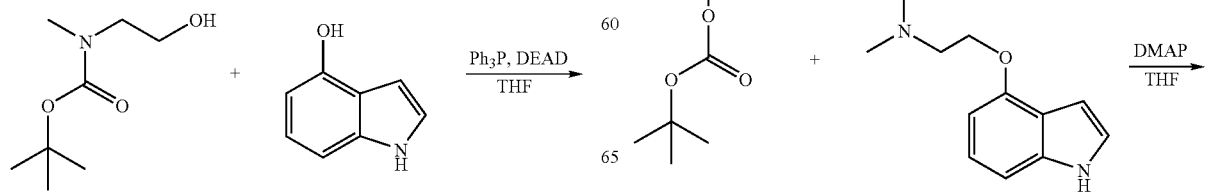

-continued

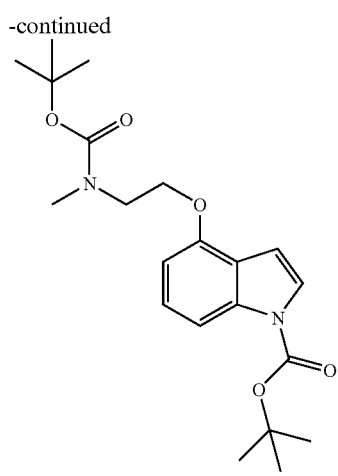

To a solution of 2-(1H-indol-4-yloxy)-ethyl]-methyl-carbamic acid tert-butyl ester (12.82 g., 44.1 mmol) in 100 mL anhydrous THF at 0° C. was added di-tert-butyldicarbonate (10.59 g., 48.5 mmol) and dimethyl-pyridin-4-yl amine (1.07 g., 8.8 mmol). The solution was stirred for 1 hour at 0° C., allowed to warm to ambient temperature and then stirred for 1 hour. The reaction mixture was washed with saturated aqueous sodium bicarbonate solution (1×45 mL), water (1×45 mL) and brine (1×45 mL). The organic fraction was dried over MgSO$_4$ and concentrated in vacuo to give a crude residue which was purified by flash chromatography (pure hexanes—90:10 hexanes:EtOAc over 30 minutes), giving 10.46 g. of 4-[2-(tert-butoxycarbonyl-methyl-amino)-ethoxy]-indole-1-carboxylic acid tert-butyl ester as a clear oil. MS: 233 (M+H)$^+$.

Step 3

2-benzenesulfonyl-4-[2-(tert-butoxycarbonyl-methyl-amino)-ethoxy]-indole-1-carboxylic Acid Tert-butyl Ester

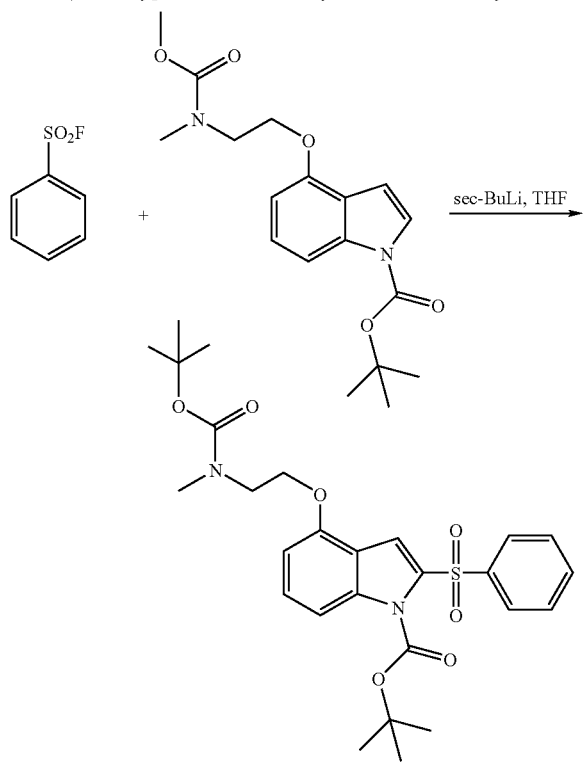

A dry 2-neck flask equipped with a magnetic stirrer was charged with 4-[2-(tert-butoxycarbonyl-methyl-amino)-ethoxy]-indole-1-carboxylic acid tert-butyl ester from Step 2 and purged with N$_2$. Freshly distilled THF (40 mL) was added via syringe and the system was cooled to −78° C. in a bath of dry ice in acetone. To this solution was added sec-butyl lithium (2.9 mL of a 1.3 M solution in hexanes, 3.9 mmol) drop-wise via syringe over 5 minutes. The solution was stirred at −78° C. under N$_2$ for 1 hour. Benzenesulfonyl fluoride was then added drop-wise via syringe over 5 minutes. The temperature was maintained at −78° C. while the solution was stirred for 1 hour. The solution was then allowed to warm to ambient temperature and was quenched by the addition of saturated ammonium chloride solution (45 mL in three portions). The layers were separated, and the aqueous layer was extracted with ethyl acetate (2×30 mL). The combined organic fractions were washed with saturated ammonium chloride (1×45 mL), water (1×45 mL), brine (1×45 mL), dried over MgSO$_4$ and concentrated in vacuo. The crude residue was purified by flash chromatography (90:10 hexanes:EtOAc-80:20 hexanes:EtOAc over 30 minutes) to give 0.250 g. 2-benzenesulfonyl-4-[2-(tert-butoxycarbonyl-methyl-amino)-ethoxy]-indole-1-carboxylic acid tert-butyl ester as a yellow foam. MS: 553 (M+N)$^+$.

Step 4

[2-(2-benzenesulfonyl-1H-indol-4-yloxy)-ethyl]-methyl-amine Hydrochloride

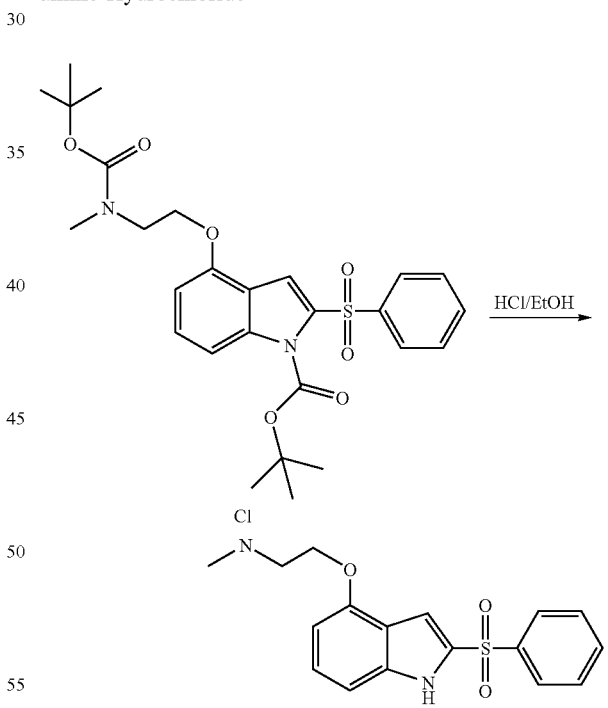

2-Benzenesulfonyl-4-[2-(tert-butoxycarbonyl-methyl-amino)-ethoxy]-indole-1-carboxylic acid tert-butyl ester (0.250 g., 0.5 mmol) from Step 3 was dissolved in 5 mL EtOH. To this solution was added 1 mL of 2M ethanolic hydrogen chloride solution. The reaction mixture was heated at 100° C. for 35 minutes. Upon cooling to ambient temperature, a fine white precipitate was observed. After filtration and drying in vacuo at 60° C., [2-(2-benzenesulfonyl-1H-indol-4-yloxy)-ethyl]-methyl-amine hydrochloride was obtained. MS: 330 (M+H)$^+$, mp=250.7–252.1° C.

Example 5

[2-(2-benzenesulfonyl-1H-indol-7-yloxy)-ethyl]-methyl-amine Hydrochloride

This example illustrates a method for producing [2-(2-benzenesulfonyl-1H-indol-7-yloxy)-ethyl]-methyl-amine hydrochloride and other substituted indole compounds in accordance with the invention using the synthetic procedure outlined below in Scheme G.

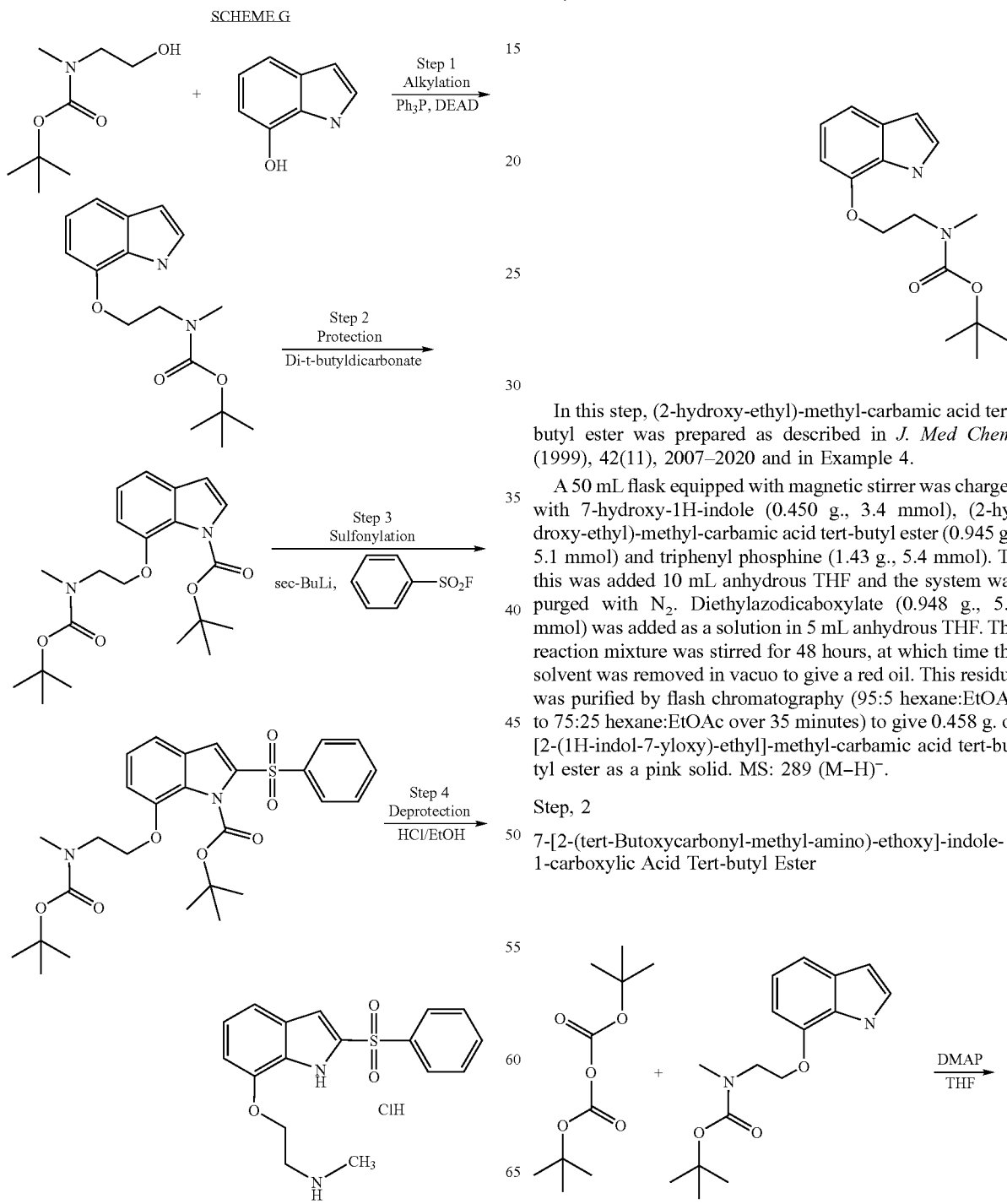

Step 1

[2-(1H-indol-7-yloxy)-ethyl]-methyl-carbamic Acid Tert-butyl Ester

In this step, (2-hydroxy-ethyl)-methyl-carbamic acid tert-butyl ester was prepared as described in *J. Med Chem.* (1999), 42(11), 2007–2020 and in Example 4.

A 50 mL flask equipped with magnetic stirrer was charged with 7-hydroxy-1H-indole (0.450 g., 3.4 mmol), (2-hydroxy-ethyl)-methyl-carbamic acid tert-butyl ester (0.945 g., 5.1 mmol) and triphenyl phosphine (1.43 g., 5.4 mmol). To this was added 10 mL anhydrous THF and the system was purged with $N_2$. Diethylazodicaboxylate (0.948 g., 5.4 mmol) was added as a solution in 5 mL anhydrous THF. The reaction mixture was stirred for 48 hours, at which time the solvent was removed in vacuo to give a red oil. This residue was purified by flash chromatography (95:5 hexane:EtOAc to 75:25 hexane:EtOAc over 35 minutes) to give 0.458 g. of [2-(1H-indol-7-yloxy)-ethyl]-methyl-carbamic acid tert-butyl ester as a pink solid. MS: 289 (M–H)⁻.

Step, 2

7-[2-(tert-Butoxycarbonyl-methyl-amino)-ethoxy]-indole-1-carboxylic Acid Tert-butyl Ester -continued

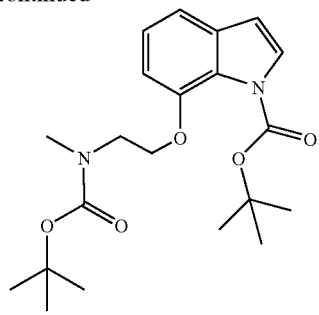

To a solution [2-(1H-indol-7-yloxy)-ethyl]-methyl-carbamic acid tert-butyl ester (2.05 g., 7.1 mmol) in 10 mL anhydrous THF at 0° C. was added di-tert-butyldicarbonate (1.68 g., 7.7 mmol) and dimethyl-pyridin-4-yl amine (0.173 g., 1.4 mmol). The solution was stirred for 1 hour at 0° C., allowed to warm to ambient temperature and then stirred for 1 hour. The reaction mixture was washed with saturated aqueous sodium bicarbonate solution (1×45 mL), water (1×45 mL) and brine (1×45 mL.) The organic fraction was dried over MgSO$_4$ and concentrated in vacuo to give a crude residue which was purified by flash chromatography (pure hexanes-90:10 hexanes:EtOAc over 30 minutes), giving 2.603 g. of 7-[2-(tert-Butoxycarbonyl-methyl-amino)-ethoxy]-indole-1-carboxylic acid tert-butyl ester as a clear oil which solidifies on standing to a white solid. mp: 74–76° C.

Step 3

2-Benzenesulfonyl-7-[2-(tert-butoxycarbonyl-methyl-amino)-ethoxy]-indole-1-carboxylic Acid Tert-butyl Ester

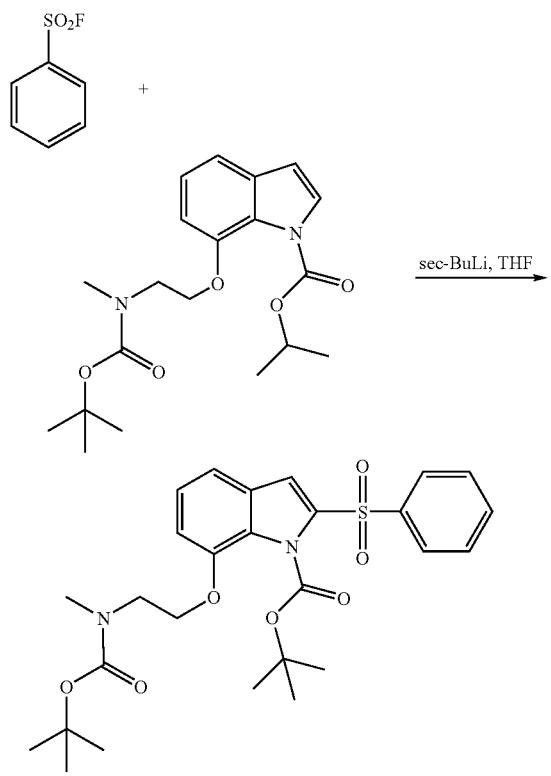

A dry 2-neck flask equipped with a magnetic stirrer was charged with 7-[2-(tert-Butoxycarbonyl-methyl-amino)-ethoxy]-indole-1-carboxylic acid tert-butyl ester (1.02 g., 2.5 mmol) and purged with N$_2$. Freshly distilled THF (40 mL) is added via syringe and the system was cooled to −78° C. in a bath of dry ice in acetone. To this solution was added sec-butyl lithium (2.3 mL of a 1.3 M solution in hexanes, 3.0 mmol) drop wise via syringe over 5 minutes. The solution was stirred at −78° C. under N$_2$ for 1 hour. Benzenesulfonyl fluoride (0.44 g., 2.75 mmol) was then added drop-wise via syringe over 5 minutes. The temperature was maintained at −78° C. while the solution is stirred for 1 hour. The solution was allowed to warm to ambient temperature and was quenched by the addition of saturated ammonium chloride solution (45 mL in three portions). The layers were separated, and the aqueous layer was extracted with ethyl acetate (2×30 mL.) The combined organic fractions were washed with saturated ammonium chloride (1×45 mL), water (1×45 mL), brine (1×45 mL), dried over MgSO$_4$ and concentrated in vacuo. The crude residue was purified by flash chromatography (90:10 hexanes:EtOAc-80:20 hexanes:EtOAc over 30 minutes) to give 0.230 g. 2-Benzenesulfonyl-7-[2-(tert-butoxycarbonyl-methyl-amino)-ethoxy]-indole-1-carboxylic acid tert-butyl ester as a clear glass. mp: 118–120° C.

Step 4

[2-(2-Benzenesulfonyl-1H-indol-7-yloxy)-ethyl]-methyl-amine

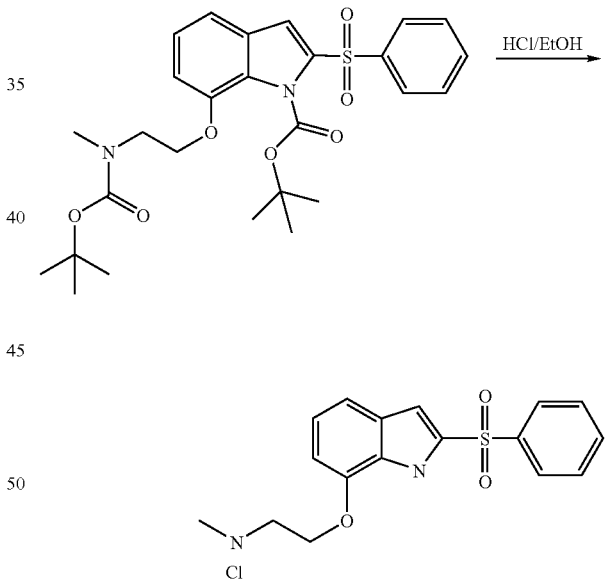

2-Benzenesulfonyl-7-[2-(tert-butoxycarbonyl-methyl-amino)-ethoxy]-indole-1-carboxylic acid tert-butyl ester (0.230 g., 0.43 mmol) from the above step was dissolved in 5 mL EtOH. To this solution was added 1 mL of 2M ethanolic hydrogen chloride solution. The reaction mixture was heated at 100° C. for 35 minutes. Upon cooling to ambient temperature, a fine white precipitate was observed. After filtration and drying in vacuo at 60° C., [2-(2-Benzenesulfonyl-1H-indol-7-yloxy)-ethyl]-methyl-amine hydrochloride was obtained as 0.140 g. white crystals. MS: 329 (M−H)$^-$, mp=289.4–291.6° C.

Example 6

2-Benzenesulfonyl-4-(2-pirrolidin-1-yl-ethoxy)-1H-indole

This example illustrates the synthesis of 2-benzenesulfonyl-4-(2-pyrrolidin-1-yl-ethoxy)-1H-indole and other substituted indoles using the synthetic procedure of Scheme H below.

SCHEME H

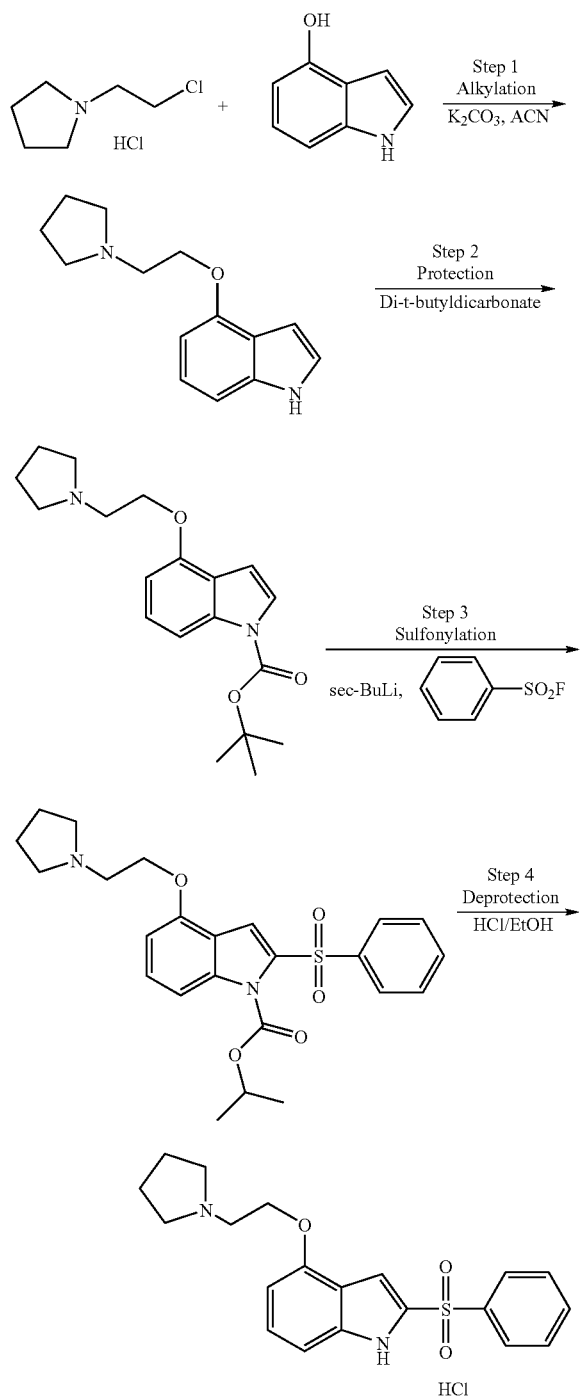

Step 1

4-(2-Pyrrolidin-1-yl-ethoxy)-1H-indole

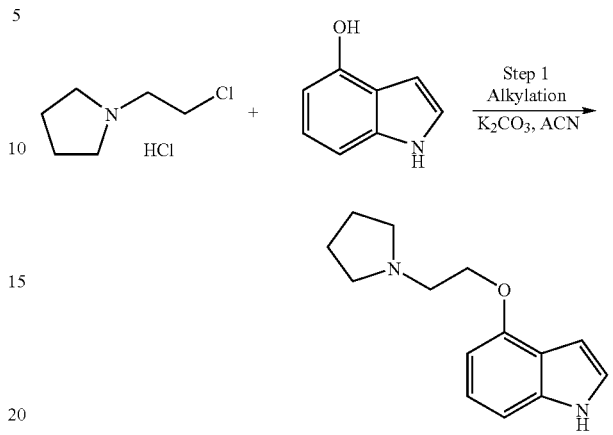

A 250 mL roundbottom flask equipped with a magnetic stirrer was charged with 4-hydroxy-1H-indole (3.85 g., 28.9 mmol) and 75 mL acetonitrile. To the resulting solution was added potassium carbonate (15.95 g., 115.6 mmol) and then 1-(2-chloro-ethyl)-pyrrolidine hydrochloride (5.41 g., 31.8 mmol). With rapid stirring, the suspension was refluxed for 72 hours and then combined with 200 mL ethyl acetate, and washed with 4×45 mL water. The aqueous fraction was washed with 4×45 mL ethyl acetate, and the combined organic fractions were washed with 50 mL brine, dried over $MgSO_4$ and concentrated in vacuo. The residue was purified by flash chromatography (0% to 40% magic base in $CH_2Cl_2$) to afford 2.209 g. of 4-(2-pyrrolidin-1-yl-ethoxy)-1H-indole. $(M+H)^+=231$.

Step 2

4-(2-Pyrrolidin-1-yl-ethoxy)-indole-1-carboxylic Acid Tert-butyl

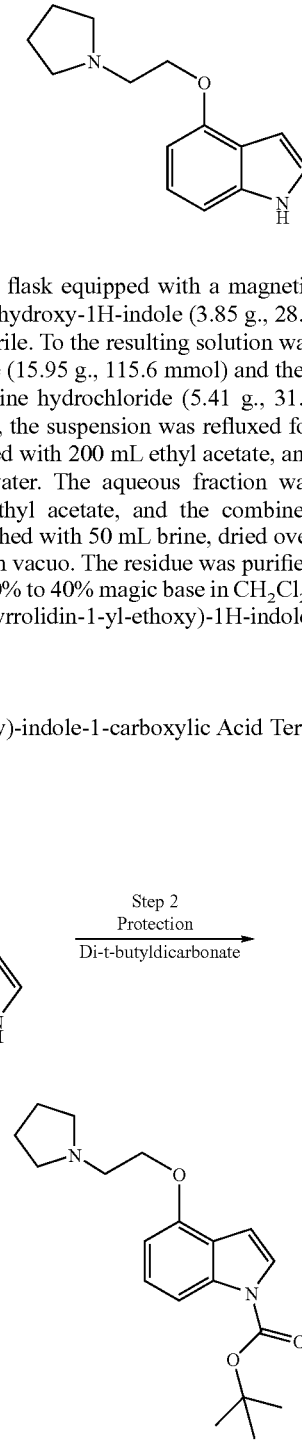

Using di-tert-butyldicarbonate as described in step 2 of Example 5 above, but with 4-(2-pyrrolidin-1-yl-ethoxy)-1H-indole instead of [2-(1H-indol-7-yloxy)-ethyl]-methyl-carbamic acid tert-butyl ester, 4-(2-pyrrolidin-1-yl-ethoxy)-indole-1-carboxylic acid tert-butyl ester was prepared: (M+H)$^+$=331.

Similarly, but replacing 4-(2-pyrrolidin-1-yl-ethoxy)-1H-indole with 3-(1H-Indol-4-yloxymethyl)-azetidine-1-carboxylic acid tert-butyl ester, 4-(1-tert-Butoxycarbonyl-azetidin-3-ylmethoxy)-indole-1-carboxylic acid tert-butyl ester was prepared: $^1$H NMR (CDCl$_3$, 300 MHz) δ: 1.46 (s, 9H), 1.47 (s, 9H), 3.04 (m, 1H), 3.89 (m, 2H), 4.09 (m, 2H), 4.20 (m, 2H), 6.66 (m, 2H), 7.20 (t, 1H, J=8.1), 7.48 (d, 1H, J=3.77), 7.78 (d, 1H, J=8.1).

Step 3

2-Benzenesulfonyl-4-(2-pyrrolidin-1-yl-ethoxy)-indole-1-carboxylic Acid Tert-butyl Ester

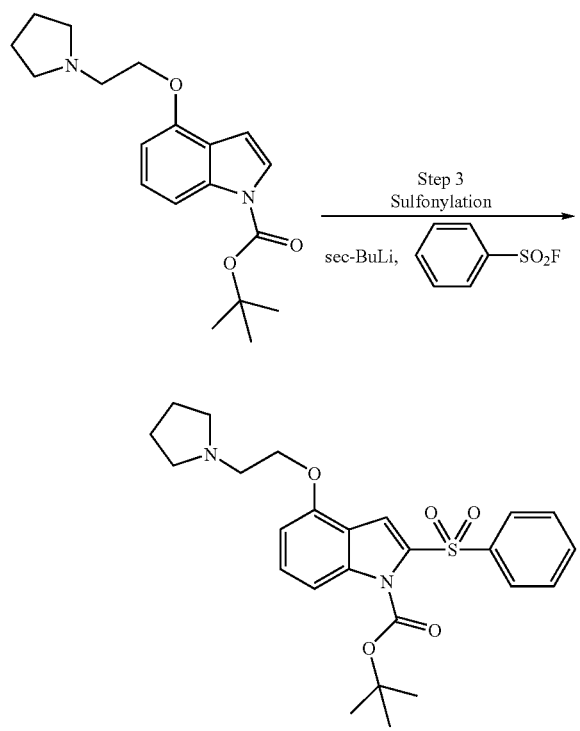

Using the procedure of step 3 from Example 5 above, but replacing 7-[2-(tert-butoxycarbonyl-methyl-amino)-ethoxy]-indole-1-carboxylic acid tert-butyl ester with 4-(2-pyrrolidin-1-yl-ethoxy)-indole-1-carboxylic acid tert-butyl ester, 2-benzenesulfonyl-4-(2-pyrrolidin-1-yl-ethoxy)-indole-1-carboxylic acid tert-butyl ester was prepared: (M+H)$^+$=471.

Similarly, but replacing 4-(2-pyrrolidin-1-yl-ethoxy)-indole-1-carboxylic acid tert-butyl ester with 4-(1-tert-butoxycarbonyl-azetidin-3-ylmethoxy)-indole-1-carboxylic acid tert-butyl ester, 2-benzenesulfonyl-4-(1-tert-butoxycarbonyl-azetidin-3-ylmethoxy)-indole-1-carboxylic acid tert-butyl ester was prepared: $^1$H NMR (CDCl$_3$, 300 MHz) δ: 1.46 (s, 9H), 1.56 (s, 9H), 3.05 (m, 1H), 3.82 (s, 2H), 4.16 (m, 4H), 6.68 (d, 1H, J=7.9), 7.36 (t, 1H, J=8.2), 7.53 (m, 5H), 7.96 (d, 1H, J=8.1).

Step 4

2-Benzenesulfonyl-4-(2-pyrrolidin-1-yl-ethoxy)-1H-indole

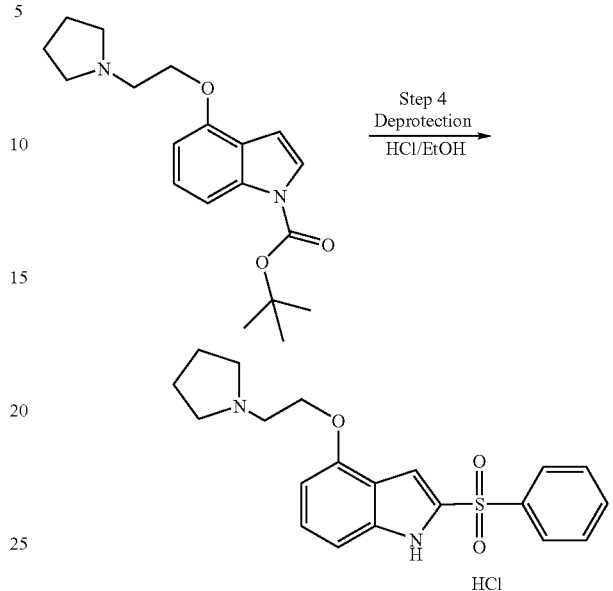

Deprotection of the indole nitrogen of 2-benzenesulfonyl-4-(2-pyrrolidin-1-yl-ethoxy)-indole-1-carboxylic acid tert-butyl ester using the procedure of step 4, Example 5, yielded 2-benzenesulfonyl-4-(2-pyrrolidin-1-yl-ethoxy)-1H-indole, (M+H)$^+$=371.

Similarly, deprotection of 2-benzenesulfonyl-4-(1-tert-butoxycarbonyl-azetidin-3-ylmethoxy)-indole-1-carboxylic acid tert-butyl ester afforded 4-(azetidin-3-ylmethoxy)-2-benzenesulfonyl-1H-indole: M+H)$^+$=343.

Example 7

2-[3-(2-Fluoro-benzenesulfonyl)-1H-indol-7-yloxy]-ethylamine

This example illustrates the synthesis of 2-[3-(2-Fluoro-benzenesulfonyl)-1H-indol-7-yloxy]-ethylamine using the synthetic procedure of Scheme I below.

SCHEME I

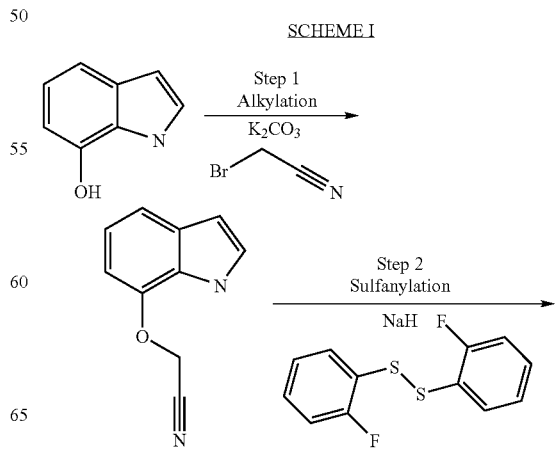

-continued

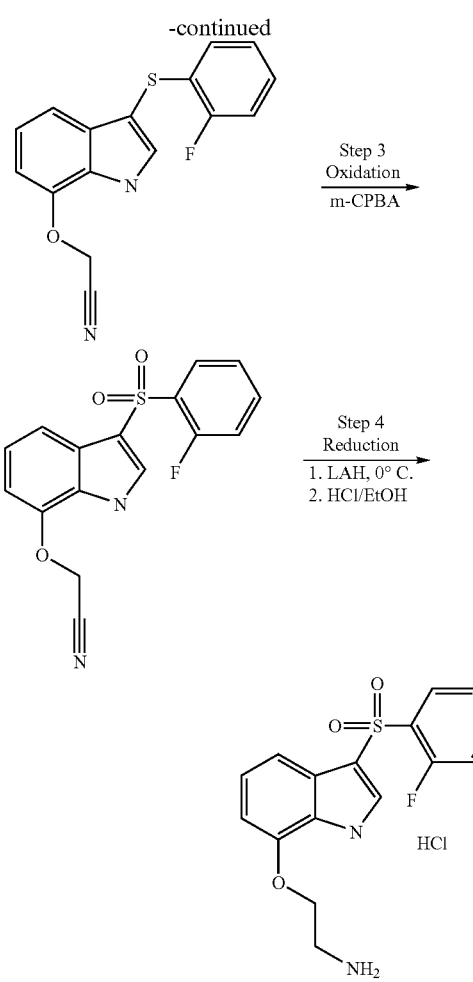

Step 1

(1H-Indol-7-yloxy)-acetonitrile

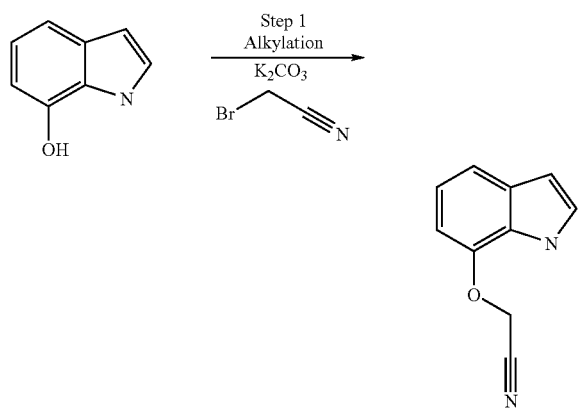

In a 100 mL roundbottom flask equipped with a magnetic stirrer and rubber septum, 7-hydroxy-1H-indole (1.66 g., 12.48 mmol) was dissolved 50 mL anhydrous acetonitrile. The flask was charged with potassium carbonate (6.88 g., 49.9 mmol) and cooled to 0° C. While stirring, bromoacetonitrile (1.64 g., 13.73 mmol) was added dropwise over two minutes. The reaction mixture was allowed to warm to ambient temperature and stirring was continued for three hours. The solution was washed with water (2×30 mL) and brine (1×30 mL), dried over MgSO₄ and concentrated in vacuo. The resulting oily brown residue was purified by flash chromatography (95:5 ethyl acetate:hexanes to 85:15 ethyl acetate:hexanes over minutes) to give (1H-Indol-7-yloxy)-acetonitrile as a crystalline solid (0.244-g.) ms: (M−H)⁻=171.2.

Step, 2

3-(2-Fluoro-phenylsulfanyl)-1H-indol-7-yloxy]-acetonitrile

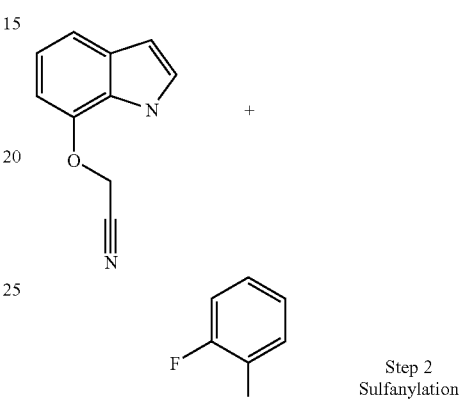

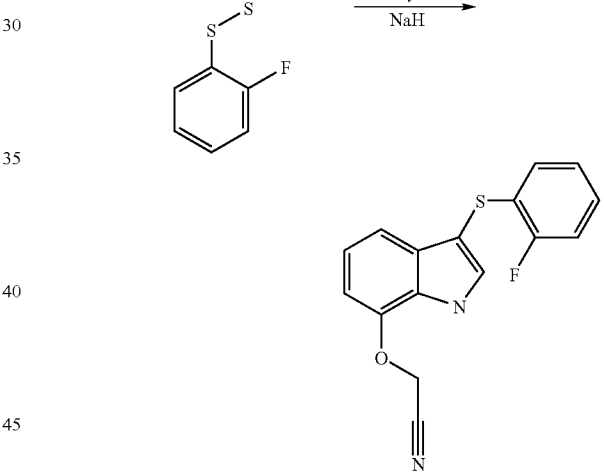

To a solution of (1H-indol-7-yloxy)-acetonitrile (0.244 g., 1.42 mmol) in 15 mL anhydrous dimethylformamide was added sodium hydride (0.062 g. of a 60% suspension in mineral oil, 1.56 mmol) portion wise). The solution was stirred with a magnetic stirrer at room temperature for 20 minutes. Bis-(2-fluorophenyl) disulfide (0.396 g., 1.56 mmol) was added in one portion and the reaction mixture was stirred at room temperature for 2 hours. The reaction mixture was partitioned between water (50 mL) and ethyl acetate (50 mL). The aqueous layer was extracted with ethyl acetate (2×25 mL) and the combined organic fractions were washed with water (2×25 mL) and brine (2×25 mL). After drying over MgSO₄, the organic fraction was concentrated in vacuo and the resulting dark red residue was purified by flash chromatography (chromatography (95:5 ethyl acetate: hexanes to 85:15 ethyl acetate:hexanes over 30 minutes) to give 0.196 g. of [3-(2-fluoro-phenylsulfanyl)-1H-indol-7-yloxy]-acetonitrile as a clear oil. ms: (M−H)⁻=297.1

Step 3

3-(2-Fluoro-benzenesulfonyl)-1H-indol-7-yloxy]-acetonitrile

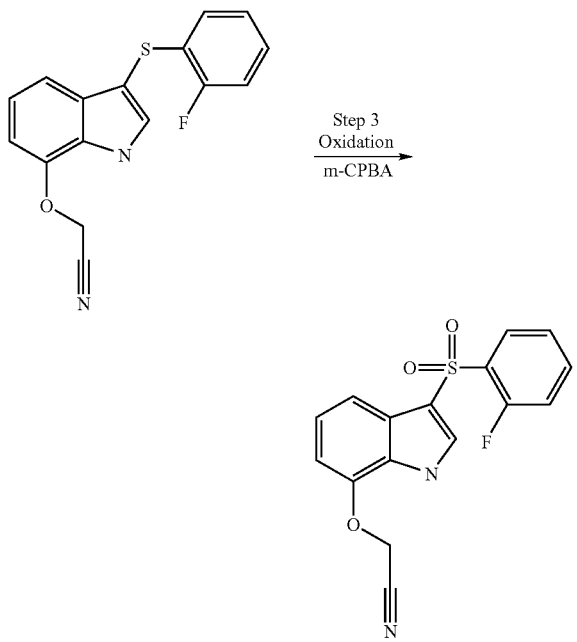

Step 3
Oxidation
m-CPBA

A 25 mL flask equipped with a magnetic stirrer was charged with a solution [3-(2-Fluoro-phenylsulfanyl)-1H-indol-7-yloxy]-acetonitrile (0.196 g., 0.657 mmol) in 25 mL of dichloromethane. This solution was cooled to 0° C. and meta-chloroperoxybenzoic acid (0.309 g., 1.38 mmol) was added portion wise over 10 minutes. The reaction mixture was allowed to warm to room temperature and stirring was continued for 2 hours. The reaction mixture was washed with 1 M potassium carbonate solution (2×45 mL) and water (1×45 mL). The organic fractions were dried over $MgSO_4$ and concentrated in vacuo. The resulting residue was purified by flash chromatography (9:1 hexanes:EtOAc to 4:1 hexanes:EtOAc over 30 minutes) to give 0.125 g. of [3-(2-fluoro-benzenesulfonyl)-1H-indol-7-yloxy]-acetonitrile as white crystals. ms: $(M-H)^-=329.1$

Step 4

2-[3-(2-Fluoro-benzenesulfonyl)-1H-indol-7-yloxy]-ethylamine Hydrochloride

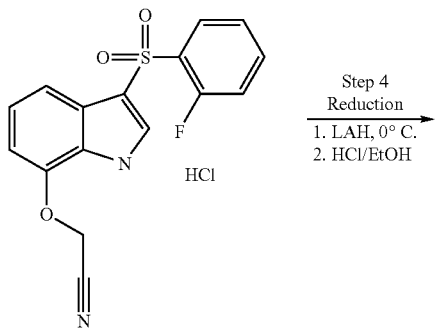

Step 4
Reduction
1. LAH, 0° C.
2. HCl/EtOH

-continued

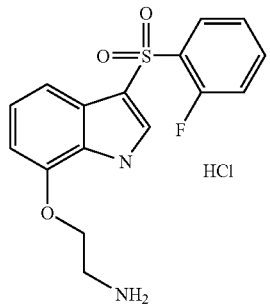

A dry 25 mL roundbottom flask was equipped with a magnetic stirrer and purged with argon gas. To this was added via syringe a solution of [3-(2-fluoro-benzenesulfonyl)-1H-indol-7-yloxy]-acetonitrile in 10 mL of anhydrous THF. The flask was cooled to 0° C. and lithium aluminum hydride solution was added (1 mL of 1M solution in THF) dropwise over 2 minutes via syringe. The reaction was allowed to warm to room temperature. After 1 hour, the reaction mixture was combined with 25 mL diethyl ether and quenched with sodium sulfate decahydrate (0.371 g., 1.14 mmol). The resulting suspension was stirred for 2 hours, filtered through a bed of celite and concentrated in vacuo. The resulting residue was purified by flash chromatography (neat $CH_2Cl_2$ to 10:1:0.1, $CH_2Cl_2$:MeOH:$NH_4OH$ over 35 minutes) to give 0.138 g. of the free base 2-[3-(2-fluoro-benzenesulfonyl)-1H-indol-7-yloxy]-ethylamine. The solid was dissolved in 1 mL ethanol, to which was added 0.5 mL of 2N ethanolic HCl. The resulting solution was concentrated in vacuo and triturated with 45 mL cold ethyl ether to give 110 mg of 2-[3-(2-Fluoro-benzenesulfonyl)-1H-indol-7-yloxy]-ethylamine hydrochloride as a purple powder (11%). $(M-H)^-=333$.

Also isolated as a minor product from the reduction of step 4 was 1-(2-Fluoro-benzenesulfonyl)-3,4-dihydro-5-oxa-2a-aza-acenaphthylen-3-ylamine, ms $(M+H)=333$.

Example 8

Formulations

Pharmaceutical preparations for delivery by various routes are formulated as shown in the following Tables. "Active ingredient" or "Active compound" as used in the Tables means one or more of the Compounds of Formula I.

| Composition for Oral Administration | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

Composition for Oral Administration

| Ingredient | % wt./wt. |
|---|---|
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

Composition for Oral Administration

| Ingredient | Amount |
|---|---|
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

Parenteral Formulation

| Ingredient | % wt./wt. |
|---|---|
| Active ingredient | 0.25 g |
| Sodium Chloride | qs to make isotonic |
| Water for injection | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Suppository Formulation

| Ingredient | % wt./wt. |
|---|---|
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Topical Formulation

| Ingredients | grams |
|---|---|
| Active compound | 0.2–2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025–0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50–100 microliters of formulation per actuation. A typical dosing schedule is 2–4 sprays every 4–12 hours.

Example 9

Radioligand Binding Studies

This example illustrates in vitro radioligand binding studies of Compound of Formula I.

The binding activity of compounds of this invention in vitro was determined as follows. Duplicate determinations of ligand affinity are made by competing for binding of [$^3$H]LSD in cell membranes derived from HEK293 cells stably expressing recombinant human 5-HT6 receptor.

All determinations were made in assay buffer containing 50 mM Tris-HCl, 10 mM MgSO$_4$, 0.5 mM EDTA, 1 mM ascorbic acid, pH 7.4 at 37° C., in a 250 microliter reaction volume. Assay tubes containing [$^3$H] LSD (5 nM), competing ligand, and membrane were incubated in a shaking water bath for 60 min. at 37° C., filtered onto Packard GF-B plates (pre-soaked with 0.3% PEI) using a Packard 96 well cell harvester and washed 3 times in ice cold 50 mM Tris-HCl. Bound [$^3$H] LSD was determined as radioactive counts per minute using Packard TopCount.

Displacement of [3H]LSD from the binding sites was quantified by fitting concentration-binding data to a 4-parameter logistic equation:

$$\text{binding} = \text{basal} + \left( \frac{B\text{max} - \text{basal}}{1 + 10^{-\text{Hill}(\log[\text{ligand}] - \log IC_{50})}} \right)$$

where Hill is the Hill slope, [ligand] is the concentration of competing radioligand and IC$_{50}$ is the concentration of radioligand producing half-maximal specific binding of radioligand. The specific binding window is the difference between the Bmax and the basal parameters.

Using the procedures of this Example, compounds of Formula I were tested and found to be selective 5-HT6 antagonists. Representative 5-HT6 affinity values. (pKi) for compounds of the invention from the above assay are shown in Table 2.

TABLE 2

| Compound | pKi |
| --- | --- |
| 3-Benzenesulfonyl-7-(2-pyrrolidin-1-yl-ethoxy)-1H-indole | 7.7 |
| 3-(3-Chloro-benzenesulfonyl)-7-(2-pyrrolidin-1-yl-ethoxy)-1H-indole | 8.3 |
| 3-(2-Chloro-benzenesulfonyl)-7-(2-pyrrolidin-1-yl-ethoxy)-1H-indole | 8.4 |
| 3-(3,4-Dichloro-benzenesulfonyl)-7-(2-pyrrolidin-1-yl-ethoxy)-1H-indole | 7.7 |
| 3-(2,5-Dichloro-benzenesulfonyl)-7-(2-pyrrolidin-1-yl-ethoxy)-1H-indole | 8.2 |

Example 10

Cognition Enhancement

The cognition-enhancing properties of compounds of the invention may be in a model of animal cognition: the object recognition task model. 4-month-old male Wistar rats (Charles River, The Netherlands) were used. Compounds were prepared daily and dissolved in physiological saline and tested at three doses. Administration was always given i.p. (injection volume 1 ml/kg) 60 minutes before T1. Scopolamine hydrobromide was injected 30 minutes after compound injection. Two equal testing groups were made of 24 rats and were tested by two experimenters. The testing order of doses was determined randomly. The experiments were performed using a double blind protocol. All rats were treated once with each dose condition. The object recognition test was performed as described by Ennaceur, A., Delacour, J., 1988, A new one-trial test for neurobiological studies of memory in rats. 1: Behavioral data. *Behav. Brain Res.* 31, 47–59.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A compound of the formula I:

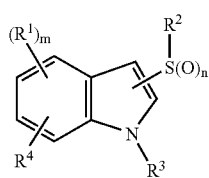

or a pharmaceutically acceptable salt or prodrug thereof, wherein:

m is from 0 to 3;
n is from 0 to 2;

each $R^1$ is independently hydrogen, halo, alkyl, haloalkyl, hydroxy, heteroalkyl, nitro, alkoxy, cyano, —$NR^aR^b$, —$S(O)_s$—$R^a$, —$C(=O)$—$NR^aR^b$, —$SO_2$—$NR^aR^b$, —$N(R^a)$—$C(=O)$—$R^b$, or —$C(=O)$—$R^a$, where each of $R^a$ and $R^b$ is independently hydrogen or alkyl, or two of $R^1$ may form an alkylene or alkylene dioxy group;

$R^2$ is aryl or heteroalkyl;
$R^3$ is hydrogen or alkyl; and
$R^4$ is of the formula:

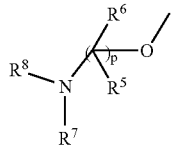

wherein:
p is 2 or 3; and
$R^5$, $R^6$, $R^7$ and $R^8$ each independently is hydrogen or alkyl, or one of $R^5$ and $R^6$ together with one of $R^7$ and $R^8$ and the atoms therebetween may form a heterocyclic ring of 4 to 7 members, or $R^7$ and $R^8$ together with their shared nitrogen may form a heterocyclic ring of 4 to 7 members; or one of $R^7$ and $R^8$ together with $R^3$ and the atoms therebetween may form a heterocyclic ring of 4 to 7 members.

2. The compound of claim 1, wherein the radical —S(O)$_n$—$R^2$ is at the 2-position of the indole ring system.

3. The compound of claim 1, wherein the radical —S(O)$_n$—$R^2$ is at the 3-position of the indole ring system.

4. The compound of claim 1, wherein $R^4$ is at the 7-position of the indole ring system.

5. The compound of claim 4, wherein $R^2$ is optionally substituted phenyl.

6. The compound of claim 4, wherein in is 0.

7. The compound of claim 4, wherein a is 2.

8. The compound or claim 4, wherein n is 0.

9. The compound of claim 4, wherein $R^2$ is 2-halophenyl, 3-halopheny, 4-halophenyl, 2,3-dihalophenyl, 2,4-dihalophenyl, 3,4-dihalophenyl, 2,5-dihalophenyl, 3,5-dihalophenyl, 2-alkoxyphenyl, 3-alkoxypheny, 4-alkoxyphenyl, 2,3-dialkoxyphenyl, 2,4-dialkoxyphenyl, 3,4-dialkoxyphenyl, 3,5-dialkoxyphenyl, or 2,5-dialkoxyphenyl.

10. The compound of claim 4, wherein $R^2$ is 4-chlorophenyl, 2,3-dichlorophenyl, 2-chlorophenyl, 2-fluorophenyl, 3-fluorophenyl, or 2-methoxyphenyl.

11. The compound of claim 4, wherein $R^4$ is optionally substituted 2-pyrrolidin-1-yl-ethoxy, optionally substituted pyrrolidin-2-methoxy, optionally substituted piperidin-4-yloxy, optionally substituted azetidin-3-yl-methoxy, aminoethoxy, methylaminoethoxy or dimethylamninoethoxy.

12. The compound of claim 4, wherein p is 2 and $R^5$ and $R^6$ are hydrogen.

13. The compound of claim 12, wherein $R^7$ and $R^8$ together form a five- or six-membered ring.

14. The compound of claim 12, wherein one of $R^7$ and $R^8$ is hydrogen and the other is alkyl.

15. The compound of claim 12, wherein $R^7$ and $R^8$ are alkyl.

16. The compound of claim 4, wherein p is 1, $R^5$ and $R^7$ are hydrogen, and $R^6$ and $R^8$ together form a five- or six-membered heterocyclic ring.

17. The compound of claim 1, wherein $R^4$ is at the 4-position of the indole ring system.

18. The compound of claim 17, wherein $R^2$ is optionally substituted phenyl.

19. The compound of claim 17, wherein m is 0.

20. The compound of claim 17, wherein n is 2.

21. The compound of claim 17, wherein n is 0.

22. The compound of claim 17, wherein $R^2$ is 2-halophenyl, 3-halopheny, 4-halophenyl, 2,3-dihalophenyl, 2,4-dihalophenyl, 3,4-dihalophenyl, 2,5-dihalophenyl, 3,5-dihalophenyl, 2-alkoxyphenyl, 3-alkoxypheny, 4-alkoxyphenyl, 2,3-dialkoxyphenyl, 2,4-dialkoxyphenyl, 3,4-dialkoxyphenyl, 3,5-dialkoxyphenyl, or 2,5-dialkoxyphenyl.

23. The compound of claim 17, wherein $R^2$ is 4-chlorophenyl, 2,3-dichlorophenyl, 2-chlorophenyl, 2-fluorophenyl, 3-fluorophenyl, or 2-methoxyphenyl.

24. The compound of claim 17, wherein $R^4$ is optionally substituted 2-pyrrolidin-1-yl-ethoxy, optionally substituted pyrrolidin-2-methoxy, optionally substituted piperidin-4-yloxy, methylaminoethoxy or dimethylaminoethoxy.

25. The compound of claim 3, wherein $R^4$ is at the 7-position of the indole ring system.

26. The compound of claim 25, wherein $R^2$ is optionally substituted phenyl.

27. The compound of claim 25, wherein m is 0.

28. The compound of claim 25, wherein a is 2.

29. The compound of claim 25, wherein n is 0.

30. The compound of claim 25, wherein $R^2$ is 2-halophenyl, 3-halopheny, 4-halophenyl, 2,3-dihalophenyl, 2,4-dihalophenyl, 3,4-dihalophenyl, 2,5-dihalophenyl, 3,5-dihalophenyl, 2-alkoxyphenyl, 3-alkoxypheny, 4-alkoxyphenyl, 2,3-dialkoxyphenyl, 2,4-dialkoxyphenyl, 3,4-dialkoxyphenyl, 3,5-dialkoxyphenyl, or 2,5-dialkoxyphenyl.

31. The compound of claim 25, wherein $R^2$ is 4-chlorophenyl, 2,3-dichlorophenyl, 2-chlorophenyl, 2-fluorophenyl, 3-fluorophenyl, or 2-methoxyphenyl.

32. The compound of claim 25, wherein $R^4$ is optionally substituted 2-pyrrolidin-1-yl-ethoxy, optionally substituted pyrrolidin-2-yl-methoxy, optionally substituted piperidin-4-yloxy, optionally substituted azetidin-3-yl-methoxy, aminoethoxy, methylaminoethoxy or dimethylaminoethoxy.

33. The compound of claim 25, wherein p is 2 and $R^5$ and $R^6$ are hydrogen.

34. The compound of claim 33, wherein $R^7$ and $R^8$ together form a five- or six-membered heterocyclic ring.

35. The compound of claim 33, wherein one of $R^7$ and $R^8$ is hydrogen and the other is alkyl.

36. The compound of claim 33, wherein $R^7$ and $R^8$ are alkyl.

37. The compound of claim 25, wherein p is 1, $R^5$ and $R^7$ are hydrogen, and $R^6$ and $R^8$ together farm a five- or six-membered heterocyclic ring.

38. The compound of claim 3, wherein $R^4$ is at the 4-position of the indole ring system.

39. The compound of claim 38, wherein $R^2$ is optionally substituted phenyl.

40. The compound of claim 38, wherein m is 0.

41. The compound of claim 38, wherein n is 2.

42. The compound of claim 38, wherein n is 0.

43. The compound of claim 38, wherein $R^2$ is 2-halophenyl, 3-halopheny, 4-halophenyl, 2,3-dihalophenyl, 2,4-dihalophenyl, 3,4-dihalophenyl, 2,5-dihalophenyl, 3,5-dihalophenyl, 2-alkoxyphenyl, 3-alkoxypheny, 4-alkoxyphenyl, 2,3-dialkoxyphenyl, 2,4-dialkoxyphenyl, 3,4-dialkoxyphenyl, 3,5-dialkoxyphenyl, or 2,5-dialkoxyphenyl.

44. The compound of claim 38, wherein $R^2$ is 4-chlorophenyl, 2,3-dichlorophenyl, 2-chlorophenyl, 2-fluorophenyl, 3-fluorophenyl, or 2-methoxyphenyl.

45. The compound of claim 38, wherein $R^4$ is optionally substituted 2-pyrrolidin-1-yl-ethoxy, optionally substituted pyrrolidin-2-methoxy, optionally substituted piperidin-4-yloxy, optionally substituted azetidin-3-yl-methoxy, aminoethoxy, methylaminoethoxy or dimethylaminoethoxy.

46. The compound of claim 1, wherein said compound is of the formula IV:

wherein:
m, p, $R^1$, $R^3$, $R^5$, $R^6$, $R^7$ and $R^8$ are as defined in claim 1;
q is from 0 to 4; and
each $R^9$ is independently hydrogen, halo, alkyl, haloalkyl or alkoxy.

47. The compound of claim 1, wherein said compound is of the formula VI:

wherein:
m, p, $R^1$, $R^3$, $R^5$, $R^6$, $R^7$ and $R^8$ are as defined in claim 1;
q is from 0 to 4; and
each $R^9$ is independently hydrogen, halo, alkyl, haloalkyl or alkoxy.

48. The compound of claim 1, wherein said compound is selected from:
3-Phenylsulfanyl-7-(2-pyrrolidin-1-yl-ethoxy)-1H-indole;
3-Benzenesulfonyl-7-(2-pyrrolidin-1-yl-ethoxy)-1H-indole;
3-(3-Chloro-benzenesulfonyl)-7-(2-pyrrolidin-1-yl-ethoxy)-1H-indole;
3-(4-Chloro-benzenesulfonyl)-7-(2-pyrrolidin-1-yl-ethoxy)-1H-indole;
3-(2,3-Dichloro-benzenesulfonyl)-7-(2-pyrrolidin-1-yl-ethoxy)-1H-indole;
3-(2-Chloro-benzenesulfonyl)-7-(2-pyrrolidin-1-yl-ethoxy)-1H-indole;
3-(3,4-Dichloro-benzenesulfonyl)-7-(2-pyrrolidin-1-yl-ethoxy)-1H-indole;
3-(2-Fluoro-benzenesulfonyl)-7-(2-pyrrolidin-1-yl-ethoxy)-1H-indole;
3-(3-Fluoro-benzenesulfonyl)-7-(2-pyrrolidin-1-yl-ethoxy)-1H-indole;

3-(3-Methoxy-benzenesulfonyl)-7-(2-pyrrolidin-1-yl-ethoxy)-1H-indole;
3-(2-Methoxy-benzenesulfonyl)-7-(2-pyrrolidin-1-yl-ethoxy)-1H-indole;
2-(Benzenesulfonyl-1H-indol-7-yloxy)-ethyl]-dimethyl-amine;
{2-[3-(2-Methoxy-benzenesulfonyl)-1H-indol-7-yloxy]-ethyl}-dimethyl-amine;
{2-[3-(2-Fluoro-benzenesulfonyl)-1H-indol-7-yloxy]-ethyl}-dimethyl-amine;
2-[3-(2-Fluoro-benzenesulfonyl)-1H-indol-7-yloxy{]-ethyl}-methyl-amine;
[2-(3-Benzenesulfonyl-1H-indol-7-yloxy)-ethyl]-methyl-amine;
2-(3-Benzenesulfonyl-1-methyl-1H-indol-7-yloxy)-ethyl]-methyl-amine;
(S)-3-(2-Fluoro-benzenesulfonyl)-7-(pyrrolidin-2-yl-methoxy)-1H-indole;
3-Benzenesulfonyl-7-(piperidin-4-yloxy)-1H-indole;
[2-(2-Benzenesulfonyl-1H-indol-4-yloxy)-ethyl]-methyl-amine;
2-(2-Benzenesulfonyl-1H-indol-7-yloxy)-ethyl]-methyl-amine;
3-(2,5-Dichloro-benzenesulfonyl)-7-(2-pyrrolidin-1-yl-ethoxy)-1H-indole;
2-Benzenesulfonyl-4-(2-pyrrolidin-1-yl-ethoxy)-1H-indole;
4-(Azetidin-3-ylmethoxy)-2-benzenesulfonyl-1H-indole; and
2-[3-(2-Fluoro-benzenesulfonyl)-1H-indol-7-yloxy]-ethylamine.

49. A pharmaceutical composition comprising an effective amount of the compound of claim 1 in admixture with a pharmaceutically acceptable carrier.

50. A method for producing a substituted indole, comprising:
(a) contacting an indole compound of the formula:

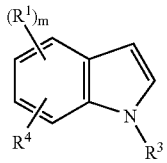

wherein:
m is from 0 to 3;
each $R^1$ is independently hydrogen, halo, alkyl, haloalkyl, hydroxy, heteroalkyl, nitro, alkoxy, cyano, —$NR^aR^b$, —$S(O)_s$—$R^a$, —C(=O)—$NR^aR^b$, —$SO_2$—$NR^aR^b$, —$N(R^a)$—C(=O)—$R^b$, or —C(=O)—$R^a$, where each of $R^a$ and $R^b$ is independently hydrogen or alkyl;
$R^3$ is hydrogen or alkyl; and:
$R^4$ is of the formula:

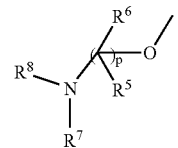

wherein:
p is from 0 to 3; and
$R^5$, $R^6$, $R^7$ and $R^8$ each independently is hydrogen or alkyl, or one of $R^5$ and $R^6$ together with one of $R^7$ and $R^8$ form a heterocyclic ring of 4 to 7 members, or $R^7$ and $R^8$ together form a heterocyclic ring of 4 to 7 members;
with a disulfide of the formula $R^2$—S—S—$R^2$ wherein $R^2$ is aryl or heteroaryl, to produce a sulfanylated indole compound of the formula:

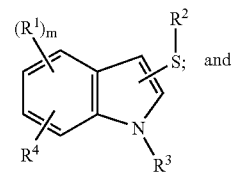

(b) optionally oxidizing the sulfanylated indole b to produce a substituted indole of the formula:

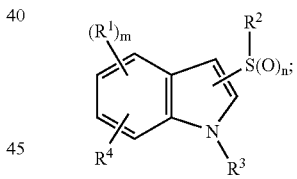

wherein n is 1 or 2.

* * * * *